US007459536B1

(12) United States Patent
Cao et al.

(10) Patent No.: US 7,459,536 B1
(45) Date of Patent: Dec. 2, 2008

(54) HGF-SF MONOCLONAL ANTIBODY COMBINATIONS

(75) Inventors: Boliang Cao, Comstock Park, MI (US); George Vande Woude, Grand Rapids, MI (US)

(73) Assignee: The United States of America as represented by the Secretary, Department of Health and Human Services, Washington, DC (US)

( * ) Notice: Subject to any disclaimer, the term of this patent is extended or adjusted under 35 U.S.C. 154(b) by 896 days.

(21) Appl. No.: 10/129,596

(22) PCT Filed: Nov. 9, 2000

(86) PCT No.: PCT/US00/31036

§ 371 (c)(1),
(2), (4) Date: Sep. 30, 2002

(87) PCT Pub. No.: WO01/34650

PCT Pub. Date: May 17, 2001

Related U.S. Application Data

(60) Provisional application No. 60/164,173, filed on Nov. 9, 1999.

(51) Int. Cl.
*C07K 16/00* (2006.01)
(52) U.S. Cl. ............ 530/387.1; 530/388.1; 530/388.24; 530/389.7
(58) Field of Classification Search .... 530/387.1–388.1
See application file for complete search history.

(56) References Cited

U.S. PATENT DOCUMENTS

| | | | | |
|---|---|---|---|---|
| 5,646,036 | A | * | 7/1997 | Schwall et al. ............ 435/252.3 |
| 5,707,624 | A | | 1/1998 | Nickoloff et al. |
| 6,852,318 | B1 | * | 2/2005 | Varner ...................... 424/130.1 |

FOREIGN PATENT DOCUMENTS

| | | |
|---|---|---|
| WO | WO 91/12272 A | 8/1991 |
| WO | WO 94/06909 A | 3/1994 |
| WO | WO 98/19696 A | 5/1998 |

OTHER PUBLICATIONS

Harlow and Lane(Antibodies, A Laboratory Manual, 1988, p. 141-142).*
Colnaghi et al. (Current Opinion in Oncology, 1993, 5:1035-1042).*
Bellusci et al., "Creation of a hepatocyte growth factor/scatter factor autocrine loop in carcinoma cells induces invasive properties associated with increased tumorigenicity," *Oncogene* 9:1091-1099 (1994).
Bussolino et al., "Hepatocyte Growth Factor is a Potent Angiogenic Factor which Stimulates Endothelial Cell Motility and Growth," *J. Cell Biol.* 119(3):629-641 (1992).
Chirgadze et al., "Crystal structure of the NK1 fragment of HGF/SF suggests a novel mode for growth factor dimerization and receptor binding," *Nat. Struct. Biol.* 6(1):72-79 (1999).
Cooper et al., "Molecular cloning of a new transforming gene from a chemically transformed human cell line," *Nature* 311(6):29-33 (1984).
Gherardi et al., "Hepatocyte Growth Factor/Scatter Factor (HGF/SF), The c-*met* Receptor and The Behaviour Epithelial Cells," *Soc. Exp. Biol.* 47:163-181 (1993).
Giordano et al., "Transfer of motogenic and invasive response to scatter factor/hepatocyte growth factor by transfection of human *MET* protooncogene," *Proc. Natl. Acad. Sci* 90:649-653 (1993).
Grant et al., "Scatter factor induces blood vessel formation in vivo," *Proc. Natl. Acad. Sci.* 90:1937-1941 (1993).
Hartmann et al., "A functional domain in the heavy chain of scatter factor/hepatocyte growth factor binds the c-*Met* receptor and induces cell dissociation but not mitogenesis," *Proc. Natl. Acad. Sci.* 89:11574-11578 (1992).
Higashio et al., "Tumor cytotoxic activity of HGF/SF," *Exper. Suppl.* 65:351-368 (1993).
Ichimura et al., "Expression of c-met/HGF receptor in human non-small cell lung carcinomas in vitro and in vivo and its prognostic significance," *Jpn. J. Cancer Res.* 87:1063-1069 (1996).
Jeffers et al., "Hepatocyte growth factor/scatter factor-Met signaling in tumorigenicity and invasion/metastasis," *J. Mol. Med.* 74:505-513 (1996).
Jeffers et al., "Autocrine hepatocyte growth factor/scatter factor-Met signaling induces transformation and the invasive/metastatic phenotype in C127 cells," *Oncogene* 13:853-861 (1996).
Kenworthy et al., "The presence of scatter factor in patients with metastic spread to the pleura," *Br. J. Cancer* 66:243-247 (1992).
Koochekpour et al., "The von Hippel-Lindau Tumor Suppressor Gene Inhibits Hepatocyte Growth Factor/Scatter Factor-Induced Invasion and Branching Morphogenesis in Renal Carcinoma Cells," *Mol. Cell. Biol.* 19(9):5902-5912 (1999).
Koochekpour et al., "Met and Hepatocyte Growth Factor/Scatter Factor Expression in Human Gliomas," *Cancer Res.* 57:5391-5398 (1997).
Lamszus et al., "Scatter Factor Promotes Motility of Human Glioma and Neuromicrovascular Endothelial Cells," *Int. J. Cancer* 75:19-28 (1998).

(Continued)

*Primary Examiner*—Karen A. Canella
*Assistant Examiner*—Peter J Reddig
(74) *Attorney, Agent, or Firm*—Ballard Spahr Andrews & Ingersoll, LLP

(57) ABSTRACT

The present invention provides a combination of anti-HGF/SF antibodies that specifically bind HGF/SF and inhibits HGF/SF activity. The present invention further provides a combination of anti-HGF/SF antibodies comprising three or more anti-HGF/SF antibodies selected from the group consisting of antibody #1 produced from hybridoma 1C10-F1-A11, antibody #4 produced from hybridoma 8H2-F2-B10, antibody #5 produced from hybridoma 13B1-E4-E10, antibody #7 produced from hybridoma 15D7-B2, and antibody #10 produced from hybridoma 31D4-C9-D4. The invention also provides a method of treating cancer in a subject comprising administering to the subject a combination of anti-HGF/SF antibodies whereby the antibodies bind to a hepatocyte growth factor, whereby the binding of the antibodies to a hepatocyte growth factor results in an inhibition of hepatocyte growth factor binding to the hepatocyte growth factor receptor, whereby the inhibition of hepatocyte growth factor binding to receptor causes an inhibition of cancer growth, thereby treating the cancer.

8 Claims, 5 Drawing Sheets

OTHER PUBLICATIONS

Liu et al., "Proto-Oncogene and Growth Factor/Receptor Expression in the Establishment of Primary Human Non-small Cell Lung Carcinoma Cell Lines," *Am. J. Pathnol.* 142(2):413-423 (1993).

Lokker et al., "Generation and Characterization of a Competitive Antagonist of Human Hepatocyte Growth Factor, HGF/NK1," *J. Biol. Chem.* 268(23):17145-17150 (1993).

Matsumoto et al., "Cooperative interaction between α- and β-Chains of Hepatocyte Growth Factor on c-Met Receptor Confers Ligand-induced Receptor Tyrosine Phosphorylation and Multiple Biological Responses," *J. Biol. Chem.* 273(36):22913-22920 (1998).

Matsumoto et al., "Roles of HGF as a pleiotropic factor in organ regeneration," Birkhauser-Verlag, Basel (1993).

Matsumoto et al., "Deletion of Kringle Domains or the N-Terminal Hairpin Structure in Hepatocyte Growth Factor Results in Marked Decreases in Related Biological Activities," *Biochem. Biophys. Res. Comm.* 181(2):691-699 (1991).

Matsumoto et al., "Hepatocyte Growth Factor: Molecular Structure, Roles in Liver Regeneration, and Other Biological Functions," *Crit. Rev. Oncog.* 3(1,2):27-54 (1992).

Montesano et al., "Identification of a Fibroblast-Derived Epithelial Morphogen as Hepatocyte Growth Factor," *Cell* 67:901-908 (1991).

Nakamura, "Structure and Function of Hepatocyte Growth Factor," *Prog. Growth Factor Res.* 367-85 (1991).

Nusrat et al., "Hepatocyte Growth Factor/Scatter Factor Effects on Epithelia. Regulation of Intercellular Junctions in Transformed and Nontransformed Cell Lines, Basolateral Polarization of c-met Receptor in Transformed and Natural Intestinal Epithelia and Induction of Rapid Wound Repair in a Transformed Model Epithelium," *J. Clin. Invest.* 93:2056-2065 (1994).

Okigaki et al., "Functional Charaacterization of Human Hepatocyte Growth Factor Mutants Obtained by Deletion of Structural Domains," *Biochemistry* 31:9555-9561 (1992).

Rong et al., "Invasiveness and metastatis of NIH 373 cells induced by Met-hepatocyte growth factor/scatter factor autocrine stimulation," *Proc. Natl. Acad. Sci.* 91:4731-4735 (1994).

Rong et al., "Met Proto-oncogene Product is Overexpressed in Tumors of p53-deficient Mice and Tumors of Li-Fraumeni Patients," *Cancer Res.* 55:1963-1970 (1995).

Rong et al., "Tumorigenesis Induced by Coexpression of Human Hepatocyte Growth Factor and the Human *met* Protooncogene Leads to High Levels of Expression of the Ligand and Receptor," *Cell Growth Differ* 4:563-569 (1993).

Rong et al., "Met Expression and Sarcoma Tumorigenicity," *Cancer Res.* 55:5355-5360 (1993).

Rong et al., "Tumorigenicity of the *met* Proto-Oncogene and the Gene for Hepatocyte Growth Factor," *Mol. Cell Biol.* 12(11)5152-5158 (1992).

Rubin et al., "Hepatocyte growth factor/ scatter factor and its receptor, the c*met* proto-oncogene product," *Biochim et Biophys. Acta* 1155:357-371 (1993).

Santos et al., "Involvement of Hepatocyte Growth Factor in Kidney Development," *Dev. Biol.* 163(2):525-529 (1994).

Schmidt et al., "Levels of Vascular Endothelial Growth Factor, Hepatocyte Growth Factor /Scatter Factor and Basic Fibroblast Growth Factor in Human Gliomas and Their Relation to Angiogenesis," *Int. J. Cancer* 84:10-18 (1999).

Shima, et al., "ELISA for F-TCF (human hepatocyte growth factor/hHGF)/ fibroblast-derived tumor cytotoxic factor antigen employing monoclonal antibodies and its application to patients with liver diseases," *Gastroen. Jap.* 26(4):477-482 (1991).

Sonnenberg et al., "Scatter Factor/Hepatocyte Growth Factor and Its Receptor, the c-met Tyrosine Kinase, Can Mediate a Signal Exchange between Mesenchyme and Epithelia during Mouse Development," *J. Cell Biol.* 123(1):223-235 (1993).

Stoker et al., "Scatter factor is a fibroblast-derived modulator of epithelial cell mobility," *Nature* 327:239-242 (1987).

Streit et al., "A role for HGF/SF in neural induction and its expression in Hensen's node during gastrulation," *Development* 121:813-824 (1995).

Tabor et al., "Monoclonal Antibodies (mAbs) to the NK1 Region of Human Hepatocyte Growth Factor (HGF) Block HGF Activity," *J. Cell Biochem.* Suppl. 18 Part A:288 (1994)(abstract).

Trusolino et al., "Interactions between scatter factors and their receptors: hints for therapeutic applications," *FASEB J.* 12(13):1267-1280 (1998).

Tsarfaty et al., "The *met* Proto-Oncogene Receptor and Lumen Formation," *Science* 257:1258-1261 (1992).

Tsarfaty et al., "The Met Proto-Oncogene Mesenchymal to Epithelial Cell Conversion," *Science* 263:98-101 (1994).

Uehara et al., "Placental defect and embryonic lethality in mice lacking hepatocyte growth factor/scatter factor," *Nature* 373:702-705 (1995).

Uehara et al. , "Expression of a Human Hepatocyte GrowthFactor/Scatter Factor cDNA in MDCK Epithelial Cells Influences Cell Morphology, Motility, and Anchorage-independent Growth," *J. Cell Biol.* 117:889-894 (1992).

Yamada et al., "Rapid and Sensitive Enzyme-Linked Immunosorbent Assay for Measurement of HGF in Rat and Human Tissues," *Biomed. Res.* 16(2):105-114 (1995).

Zaccolo et al., "Dimerization of Fab fragments enables ready screening of phage antibodies that affect hepatocyte growth factor/scatter factor activity on target cells," *Eur. J. Immunol.* 27:618-623 (1997).

* cited by examiner

HGF-SF MONOCLONAL ANTIBODY COMBINATIONS

This application claims priority to U.S. provisional application Ser. No. 60/164,173 filed on Nov. 9, 1999. The 60/164,173 provisional patent application is herein incorporated by this reference in its entirety.

BACKGROUND OF THE INVENTION

1. Field of the Invention

The present invention relates to combinations of monoclonal antibodies which specifically bind or recognize the antigen hepatocyte growth factor/scatter factor (HGF/SF) and inhibit HGF/SF activity. The application also relates to the use of the antibody in detection methods, in methods of identifying developmental disorders, and in therapy of particular conditions, such as cancer and liver disorders.

2. Background Art

HGF/SF is a heterodimeric molecule composed of an α-chain containing the N-terminal domain and four kringle domains (NK4), covalently disulfide linked to a serine protease-like β-chain. Acting through its receptor c-MET, HGF/SF initiates mitogenic, motogenic and morphogenic activities in a wide variety of cells. The N-terminal domain with the first kringle (NK1) or first two kringles (NK2) can bind to c-MET receptor with reduced affinity (10 and 4 fold respectively) when compared to wild-type HGF/SF, and both NK molecules show partial biological activity of HGF/SF (e.g., NK1 is an agonist while NK2 is an antagonist). The β-chain binds to the c-MET receptor specifically occupied with α-chain, but deletion of the β-chain results in loss of multiple biological activities of HGF/SF (1-5).

HGF/SF (hepatocyte growth factor/scatter factor) is an effector of cells expressing the Met tyrosine kinase receptor (Gherardi et al. 1993. Hepatocyte growth factor/scatter factor (HGF/SF), the c-met receptor and the behavior of epithelial cells." Symp. Soc. Exp. Biol. 47:163-181; Matsumoto et al. 1992. "Hepatocyte growth factor: molecular structure, roles in liver regeneration, and other biological functions." Crit. Rev. Oncog. 3:27-54 and Rubin et al. 1991. "Hepatocyte growth factor/scatter factor and its receptor, the c-met proto-oncogene product." Biochim. Biophys. Acta 1155: 357-371). It is produced by mesenchymal cells and acts predominantly on cells of epithelial origin in an endocrine and/or paracrine fashion (Sonnenberg et al. 1993. "Scatter factor/hepatocyte growth factor and its receptor the c-met tyrosine kinase, can mediate a signal exchange between mesenchyme and epithelia during mouse development." J. Cell Biol. 123:223-235 and Stoker et al. 1987. "Scatter factor is a fibroblast-derived modulator of epithelial cell mobility." Nature 327: 239-242). As its name implies, HGF/SF promotes the growth and/or scattering of various cell types. HGF/SF has also been shown to mediate other biological activities, including the formation of tubules (Montesano et al. 1991. "Identification of a fibroblast-derived epithelial morphogen as hepatocyte growth factor." Cell 67:901-908) and lumens (Tsarfaty et al. 1992. "The met proto-oncogene receptor and lumen formation." Science 257:1258-1261), the promotion of angiogenesis (Bussolino et al. 1992. "Hepatocyte growth factor is a potent angiogenic factor which stimulates endothelial cell motility and growth." J. Cell. Biol. 119: 629-641), the inhibition of cell growth (Higashio et al. 1993. "Tumor cytotoxic activity of HGF/SF." Exper. Suppl. 65:351-368) and the conversion from a mesenchymal to an epithelial phenotype (Tsarfaty et al. 1994. "Met mediated signaling in mesenchymal to epithelial cell conversion." Science 263:98-101). In vivo, this ligand-receptor pair is believed to play a role in neural induction (Streit et al. 1995. "A role for HGF/SF in neural induction and its expression in Hensen's node during gastrulation." Development 121:813-824), kidney development (Santos et al. 1994. "Involvement of hepatocyte growth factor in kidney development." Dev. Biol. 163:525-529), tissue regeneration (Matsumoto et al. 1993. "Roles of HGF as a pleiotropic factor in organ regeneration." Birkhauser-Verlag, Basel), wound healing (Nusrat et al. 1994. "Hepatocyte growth factor/scatter factor effects on epithelia. Regulation of intercellular junctions in transformed and nontransformed cell lines, basolateral polarization of c-met receptor in transformed and natural intestinal epithelia, and induction of rapid wound repair in a transformed model epithelium." J. Clin. Invest. 93:2056-2065) and is required for normal embryological development (Uehara et al. 1995. "Placental defect and embryonic lethality in mice lacking hepatocyte growth factor/scatter factor." Nature 373: 702-705). Decreased levels of HGF/SF could result in defective organogenesis resulting in developmental abnormalities. Conversely, increased HGF/SF-Met signaling after tissue injury, such as hepatic injury, could lead to abnormal tissue regeneration which contributes to chronic hepatitis, cirrhosis, and/or liver cancer.

HGF/SF-Met signaling is also important in tumor development and progression. Met was originally isolated as the product of a human oncogene, trp-met, which encodes an altered Met protein possessing constitutive, ligand-independent tyrosine kinase activity and transforming ability. (Cooper et al. 1984. "Molecular cloning of a new transforming gene from a chemically transformed human cell line" Nature 311:29-33). The coexpression of unaltered Met and HGF/SF molecules in the same cell, which generates an autocrine stimulatory loop, induces an oncogenic transformation of those cells. (Bellusci et al. 1994. "Creation of a hepatocyte growth factor/scatter factor autocrine loop in carcinoma cells induces invasive properties associated with increased tumorigenicity." Oncogene 9:1091-1099).

In addition to transforming cells, deregulated Met signaling in cells increases their invasiveness in vitro (Giordano et al. 1993. "Transfer of mitogenic and invasive response to scatter factor/hepatocyte growth factor by transfection of human MET protooncogene." Proc. Natl. Acad. Sci. USA 90:649-653) and metastatic potential in vivo (Rong et al. 1994. "Invasiveness and metastasis of NIH/3T3 cells induced by Met-HGF/SF autocrine stimulation." Proc. Natl. Acad. Sci. USA 91:4731-4735). HGF/SF-Met signaling also induces the invasiveness and metastatic potential of other cell types (Bellusci et al. 1994). The detection of significant levels of HGF/SF in the pleural effusion fluid of patients whose cancer had metastasized to the pleura (Kenworthy et al. 1992. "The presence of scatter factor in patients with metastatic spread to the pleura." Br. J. Cancer 66:243-247) demonstrates the involvement of HGF/SF-Met signaling in promoting metastasis in humans.

For example, although HGF/SF is synthesized by mesenchymal cells and acts predominantly on Met-expressing epithelial cells, it has been demonstrated that human sarcoma cell lines often inappropriately express high levels of Met and respond mitogenically to HGF/SF (Rong et al. 1995. "Met proto-oncogene product is overexpressed in tumors of p53-deficient mice and tumors of Li-Fraumeni patients. Cancer Res. 55:1963-1970 and Rong et al. 1993. "Met expression and sarcoma tumorigenicity." Cancer Res. 53:5355-5360). It has also been shown that clinical sarcoma samples may overexpress the Met receptor (Rong et al. 1993 and Rong et al. 1995). Studies on lung adenocarcinomas revealed increased Met staining in these tumors (Ichimura et al. 1996. "Expression of c-met/HGF receptor in human non-small cell lung carcinomas in vitro and in vivo and its prognostic significance. Jpn. J. Cancer Res. 87:1063-1069 and Liu and Tsao 1993. "Proto-oncogene and growth factor/receptor expression in the establishment of primary human non-small cell lung carcinoma cell lines. Am. J. Pathol. 142:413-423.). Thus, this receptor-ligand pair is known to be involved in human oncogenesis and HGF/SF-Met signaling dramatically induces the in vitro invasiveness and in vivo metastatic potential of cells.

Due to its involvement in tumorigenesis, organogenesis, and regeneration, it is desirable to quantify the amount of HGF present in tissues in order to diagnose abnormalities associated with irregular HGF expression.

This invention provides monoclonal antibodies that allow characterization of HGF expression in tumor tissues. The diagnostic aspects of these antibodies can be extended to the characterization of developmental abnormalities associated with HGF/SF-Met signaling such as disorders of the kidney, liver, lung, skeletal muscle and other organs. In addition to its diagnostic properties, the HGF monoclonal antibodies act as inhibitors by blocking the interaction between HGF/SF and Met. In so doing, the antibody inhibits metastasis and decreases tumorigenecity. With respect to regenerative responses, the antibody is used to prevent abnormal regeneration and its untoward effects including tumorigenesis.

This invention provides several combinations of monoclonal antibodies that act as inhibitors of the MET-HGF/SF signaling pathway. In addition, these antibodies are useful in ELISA, immunoprecipitation studies and for immunohistochemical staining of paraffin sections. Since HGF/SF is known to be an important mediator of mitogenesis (hepatocytes), motogenesis (cell motility) and morphogenesis, and is involved in embryonic development, wound-healing, tissue organ regeneration, angiogenesis and carcinogenesis (7-10), these neutralizing Mabs are useful for a broad range of biomedical research activities and clinical applications.

SUMMARY OF THE INVENTION

The present invention provides a combination of anti-HGF/SF antibodies that specifically bind HGF/SF and inhibits HGF/SF activity.

The present invention further provides a combination of anti-HGF/SF antibodies comprising three or more anti-HGF/SF antibodies selected from the group consisting of: antibody #1 produced from hybridoma 1C10-F1-A11, antibody #4 produced from hybridoma 8H2-F2-B10, antibody #5 produced from hybridoma 13B1-E4-E10, antibody #7 produced from hybridoma 15D7-B2, and antibody #10 produced from hybridoma 31D4-C9-D4. Throughout the present application, antibody #1 is also described as antibody A.1, antibody #4 is also described as antibody A.4, antibody #5 is also described as antibody A.5, antibody #7 is also described as antibody A.7 and antibody #10 is also described as antibody A.10.

The invention also provides a method of treating cancer in a subject comprising administering to the subject a combination of anti-HGF/SF antibodies whereby the antibodies bind to a hepatocyte growth factor, whereby the binding of the antibodies to a hepatocyte growth factor results in an inhibition of hepatocyte growth factor binding to the hepatocyte growth factor receptor, whereby the inhibition of hepatocyte growth factor binding to receptor causes an inhibition of cancer growth, thereby treating the cancer.

The invention further provides a method of screening a subject for the presence of a developmental disorder comprising: contacting a tissue sample from the subject with a combination of anti-HGF/SF antibodies, detecting the binding of the antibodies with an antigen in the tissue sample, whereby a reduction in binding of antigen to the antibodies in the tissue sample relative to the binding of antigen from a control tissue sample to the antibodies indicates a decreased amount of hepatocyte growth factor in the sample, whereby the reduction in the amount of hepatocyte growth factor indicates a developmental disorder is present in the patient, thereby screening the subject for the presence of a developmental disorder.

The invention also provides a method of determining the progression of cancer comprising: contacting a tissue sample from a patient having a cancer with a combination of anti HGF/SF antibodies, detecting the binding of the antibodies with an antigen, measuring the amount of antigen in the sample, and correlating the binding of the antibodies with the antigen with a clinically defined stage of cancer development, thereby determining the progression of cancer in the patient.

The invention also provides a method of detecting the presence of cancer in a patient comprising: contacting a tissue sample from the subject with a combination of anti-HGF/SF antibodies, detecting the binding of the antibodies with an antigen in the sample, whereby an increased binding of antigen to the antibodies relative to the binding of antigen from a control tissue sample to the antibodies indicates an increased amount of hepatocyte growth factor in the sample, whereby the increased amount of hepatocyte growth factor indicates the presence of cancerous tissue in the sample, thereby detecting the presence of cancer in the patient.

DETAILED DESCRIPTION OF THE INVENTION

Figure 1A:
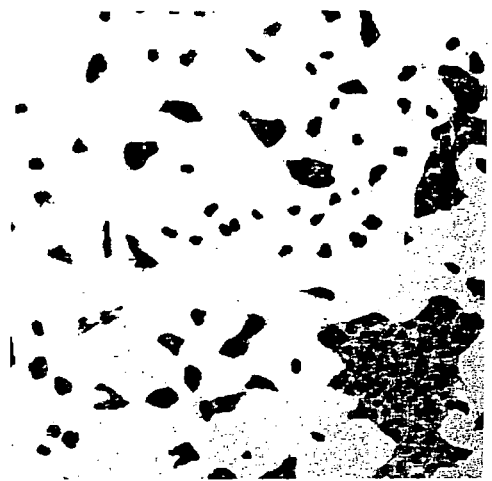
FIG. 1. Neutralization of HGF/SF mediated MDCK cell scattering. A: MDCK cells only. B: Human HGF/SF (20 ng/ml). C: Human HGF/SF (20 ng/ml) plus Mabs A.1, 5, 7 (1 ug/ml). D: Human HGF/SF (20 ng/ml) plus Mabs 7-2, 3, 4 (30 ug/ml).
Figure 1B:
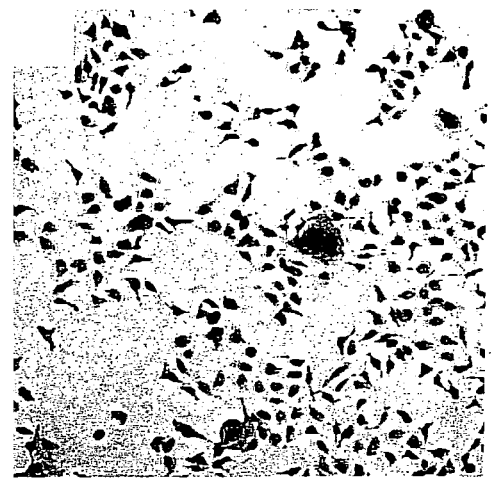
Figure 1C:
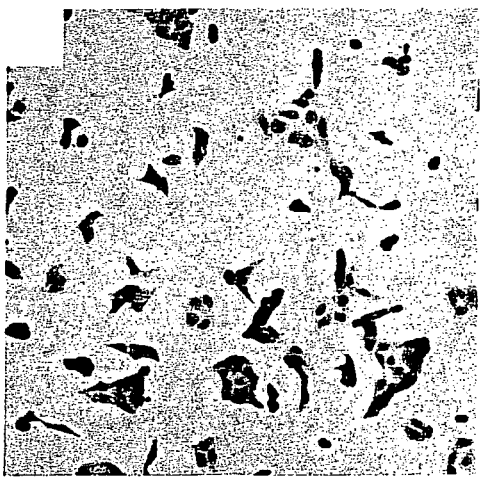
Figure 1D:
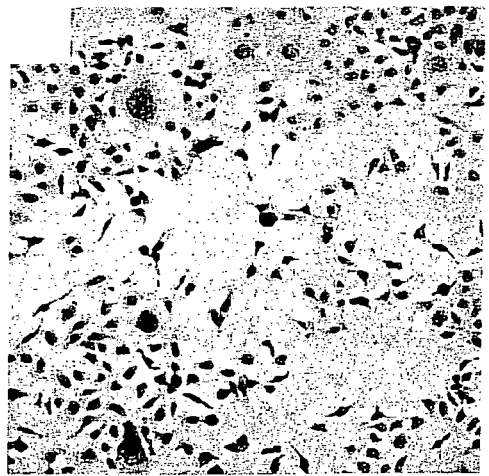
Figure 2A:
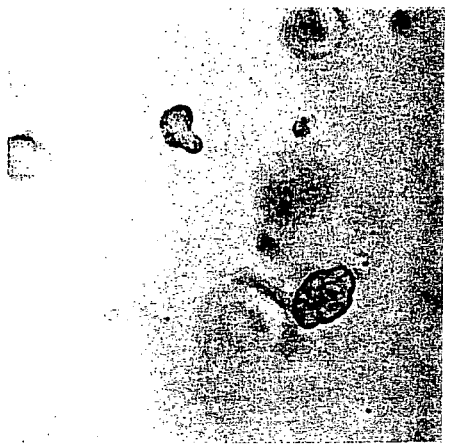
FIG. 2. Neutralization of HGF/SF mediated SK-LMS-1 cells branching morphogenesis. A: SK-LMS-1 cells only. B: Human HGF/SF (250 ng/ml). C: Human HGF/SF (250 ng/ml) plus Mabs A.1, 5, 7 (8 ug/ml). D: Human HGF/SF (250 ng/ml) plus Mabs 7-2, 3, 4 (32 ug/ml).
Figure 2B:
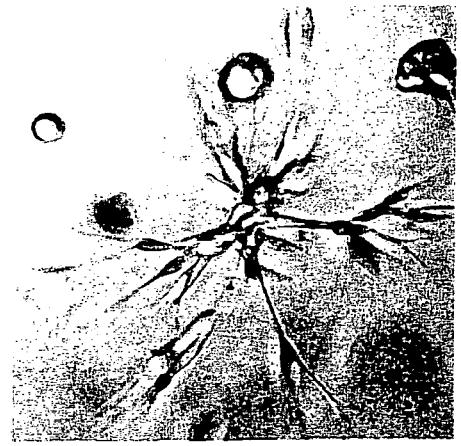
Figure 2C:
Figure 2D:
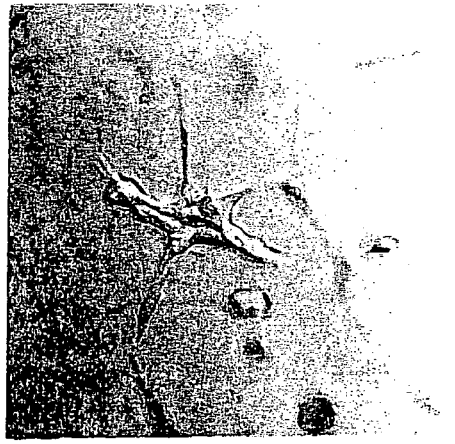

The present invention may be understood more readily by reference to the following detailed description of the preferred embodiments of the invention.

Before the present methods are disclosed and described, it is to be understood that this invention is not limited to specific compounds and methods, as such may of course, vary. It is also to be understood that the terminology used herein is for the purpose of describing particular embodiments only and is not intended to be limiting.

It must be noted that, as used in the specification and the appended claims, the singular forms "a," "an," and "the" include plural referents unless the context clearly dictates otherwise. For example, a cell can mean a single cell or more than one cell.

As used herein, the terms "hepatocyte growth factor" and "HGF" refer to a growth factor typically having a structure with six domains (finger, Kringle 1, Kringle 2, Kringle 3, Kringle 4 and serine protease domains). Fragments of HGF constitute HGF with fewer domains and variants of HGF may have some of the domains of HGF repeated; both are included if they still retain their respective ability to bind a HGF receptor. The terms "hepatocyte growth factor" and "HGF" include hepatocyte growth factor from humans ("huHGF") and any non-human mammalian species, and in particular rat HGF. The terms as used herein include mature, pre, pre-pro, and pro forms, purified from a natural source, chemically synthesized or recombinantly produced. Human HGF is encoded by the cDNA sequence published by Miyazawa et al., 1989 ("Molecular Cloning and Sequence Analysis of cDNA for Human Hepatocyte Growth Factor" Biochem. & Biophys. Res. Comm. 163:967-973), or Nakamura et al., 1989 ("Molecular Cloning and Expression of Human Hepatocyte Growth Factor" Nature 342:440-443). The sequences reported by Miyazawa et al. and Nakamura et al. differ in 14 amino acids. The reason for the differences is not entirely clear; polymorphism or cloning artifacts are among the possibilities. Both sequences are specifically encompassed by the foregoing terms. It will be understood that natural allelic variations exist and can occur among individuals, as demonstrated by one or more amino acid differences in the amino acid sequence of each individual. The terms "hepatocyte growth factor" and "HGF" specifically include the delta5 huHGF as disclosed by Seki et al. ("Isolation and Expression of cDNA for Different Forms of Hepatocyte Growth Factor from Human Leukocyte" Biochem. and Biophys. Res. Commun. 172:321-327 (1990)) and the variants disclosed by Rubin et al. ("A broad-spectrum human lung fibroblast-derived mitogen is a variant of hepatocyte growth factor" PNAS 88:415-419 (1991) and "Identification of a competitive HGF antagonist encoded by an alternative transcript" Science 254: 1382-5 (1991).

The terms "hepatocyte growth factor receptor" and "Met" when used herein refer to a cellular receptor for hepatocyte growth factor (HGF), which typically includes an extracellular domain, a transmembrane domain and an intracellular domain, as well as variants and fragments thereof which retain the ability to bind HGF. The terms "hepatocyte growth factor receptor" and "Met" include the polypeptide molecule that comprises the full-length, native amino acid sequence encoded by the gene known as p190. The present definition specifically encompasses soluble forms of HGF receptor, and HGF receptor from natural sources, synthetically produced in vitro or obtained by genetic manipulation including methods of recombinant DNA technology. The HGF receptor variants or fragments preferably share at least about 65% sequence homology, and preferably at least about 75% sequence homology more preferably at least about 85% sequence homology and most preferably at least about 95% sequence homology with any domain of the human Met amino acid sequence published in Rodrigues et al., Mol. Cell. Biol., 11:2962-2970 (1991); Park et al., Proc. Natl. Acad. Sci., 84:6379-6383 (1987); or Ponzetto et al., Oncogene, 6:553-559 (1991).

The present invention provides a combination of anti-HGF/SF monoclonal antibodies that specifically bind HGF/SF and inhibit HGF/SF activity. The term "HGF/SF activity" when used herein refers to any mitogenic, motogenic or morphogenic activities of HGF or any activities occurring as a result of HGF binding to a HGF receptor.

The term "inhibition" or "inhibit" is familiar to one skilled in the art and is used herein to describe any compound or composition which alters HGF activity. Preferably, inhibition refers to a decrease in HGF/SF activity. The degree of inhibition does not have to be complete, such as completely inhibiting HGF activity. Therefore inhibition comprises any inhibition of the activity of HGF relative to the activity of HGF in a similar environment in the absence of an inhibiting compound such as a combination of monoclonal antibodies of the present invention.

The present invention also provides a combination of anti-HGF/SF antibodies comprising three or more anti-HGF/SF antibodies selected from the group consisting of: antibody #1 produced from hybridoma 1C10-F1-A11, antibody #4 produced from hybridoma 8H2-F2-B10, antibody #5 produced from hybridoma 13B1-E4-E10, antibody #7 produced from hybridoma 15D7-B2, and antibody #10 produced from hybridoma 31D4-C9-D4. Hybridoma 1C10-F1-A11 was deposited with the American Type Culture Collection (ATCC) (10801 University Boulevard, Manassas, Va. 20110) on May 30, 2001 under ATCC Accession No. PTA-3414. Hybridoma 8H2-F2-B10 was deposited with the ATCC on May 30, 2001 under ATCC Accession No. PTA-3415. Hybridoma 13B1-E4-E10 was deposited with the ATCC on May 30, 2001 under ATCC Accession No. PTA-3416. Hybridoma 15D7-B2 was deposited with the ATCC on May 30, 2001 under ATCC Accession No. PTA-3413. Hybridoma 31D4-C9-D4 was deposited with the ATCC on May 30, 2001 under ATCC Accession No. PTA-3412.

In a preferred embodiment, this invention provides a combination of anti-HGF/SF monoclonal antibodies that specifically bind HGF/SF and inhibit HGF/SF activity, comprising antibody #1 produced from hybridoma 1C10-F1-A11, antibody #5 produced from hybridoma 13B1-E4-E10 and antibody #7 produced from hybridoma 15D7-B2.

In yet another embodiment, this invention provides a combination of anti-HGF/SF monoclonal antibodies that specifically bind HGF/SF and inhibit HGF/SF activity, comprising antibody #1 produced from hybridoma 1C10-F1-A11, antibody #4 produced from hybridoma 8H2-F2-B10 and antibody #7 produced from hybridoma 15D7-B2.

In yet another embodiment, this invention provides a combination of anti-HGF/SF monoclonal antibodies that specifically bind HGF/SF and inhibit HGF/SF activity, comprising antibody #1 produced from hybridoma 1C10-F1-A11, antibody #4 produced from hybridoma 8H2-F2-B10, antibody #5 produced from hybridoma 1C10-F1-A11 and antibody #7 produced from hybridoma 15D7-B2.

Also provided by this invention is a combination of anti-HGF/SF monoclonal antibodies that specifically bind HGF/SF and inhibit HGF/SF activity, comprising antibody #1 produced from hybridoma 1C10-F1-A11, antibody #5 produced from hybridoma 13B1-E4-E10 and antibody #10 produced from hybridoma 31D4-C9-D4.

Further provided by the present invention is a combination of anti-HGF/SF monoclonal antibodies that specifically bind HGF/SF and inhibit HGF/SF activity, comprising antibody #1 produced from hybridoma 1C10-F1-A11, antibody #4 produced from hybridoma 8H2-F2-B10 and antibody #10 produced from hybridoma 31D4-C9-D4.

Also provided by the present invention is a combination of anti-HGF/SF monoclonal antibodies that specifically bind HGF/SF and inhibit HGF/SF activity, comprising antibody #1 produced from hybridoma 1C10-F1-A11, antibody #4 produced from hybridoma 8H2-F2-B10, antibody #5 produced from hybridoma 13B1-E4-E10 and antibody #10 produced from hybridoma 31D4-C9-D4.

Also provided by this invention is anti-HGF/SF monoclonal antibody A.1 produced from hybridoma 1C10-F1-A11 and a composition comprising anti-HGF/SF monoclonal antibody A.1 produced from hybridoma 1C10-F1-A11.

Also provided by this invention is anti-HGF/SF monoclonal antibody A.4 produced from hybridoma 8H2-F2-B10 and a composition comprising anti-HGF/SF monoclonal antibody A.4 produced from hybridoma 8H2-F2-B10.

Also provided by this invention is anti-HGF/SF monoclonal antibody A.5 produced from hybridoma 13B1-E4-E10 and a composition comprising anti-HGF/SF monoclonal antibody A.5 produced from hybridoma 13B1-E4-B10.

Also provided by this invention is anti-HGF/SF monoclonal antibody A.7 produced from hybridoma 15D7-B2 and a composition comprising anti-HGF/SF monoclonal antibody A.7 produced from hybridoma 15D7-B2.

Also provided by this invention is anti-HGF/SF monoclonal antibody A.10 produced from hybridoma 31D4-C9-D4 and a composition comprising anti-HGF/SF monoclonal antibody A.10 produced from hybridoma 31D4-C9-D4.

The invention provides compositions comprising each combination of antibodies described herein.

The term "antibodies" is used herein in a broad sense and includes intact immunoglobulin molecules and fragments or polymers of those immunoglobulin molecules, so long as they exhibit any of the desired properties described herein. Antibodies are typically proteins which exhibit binding specificity to a specific antigen. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (κ) and lambda (λ), based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called alpha, delta, epsilon, gamma, and mu, respectively.

The term "variable" is used herein to describe certain portions of the variable domains which differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat E. A. et al., "Sequences of Proteins of Immunological Interest" National Institutes of Health, Bethesda, Md. (1987)). The constant domains are not involved directly in binding an antibody to an antigen, but exhibit various effector functions, such as participation of the antibody in antibody-dependent cellular toxicity.

The term "monoclonal antibody" as used herein refers to an antibody obtained from a substantially homogeneous population of antibodies, i.e., the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity (See, U.S. Pat. No. 4,816,567 and Morrison et al., Proc. Natl. Acad. Sci. USA, 81:6851-6855 (1984)).

Monoclonal antibodies of the invention may be prepared using hybridoma methods, such as those described by Kohler and Milstein, Nature, 256:495 (1975). In a hybridoma method, a mouse or other appropriate host animal, is typically immunized with an immunizing agent to elicit lymphocytes that produce or are capable of producing antibodies that will specifically bind to the immunizing agent. Alternatively, the lymphocytes may be immunized in vitro.

Preferably, the immunizing agent includes the HGF/SF polypeptide or a fusion protein thereof. The immunizing agent may alternatively comprise a fragment or portion of HGF having one or more amino acid residues that participate in the binding of HGF to its receptor.

Generally, peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, "Monoclonal Antibodies: Principles and Practice" Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies (Kozbor, J. Immunol., 133:3001 (1984) and Brodeur et al., "Monoclonal Antibody Production Techniques and Applications" Marcel Dekker, Inc., New York, (1987) pp. 51-63).

The culture medium in which the hybridoma cells are cultured can then be assayed for the presence of monoclonal antibodies directed against HGF. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art, and are described further in the Examples below. The binding affinity of the monoclonal antibody can, for example, be determined by the Scatchard analysis of Munson et al., Anal. Biochem., 107:220 (1980).

After the desired hybridoma cells are identified, the clones may be subcloned by limiting dilution procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody comprising one antigen-combining site having specificity for a HGF and another antigen-combining site having specificity for a different antigen, such as HER2 or CD3.

Monovalent antibodies are also contemplated by this invention and may be capable of interfering with HGF, its fragments or its variants binding to the HGF receptor, such as by sterically hindering access of HGF, its fragments or its variants to the receptor.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

An isolated immunogenically specific epitope or fragment of the antibody is also provided. A specific immunogenic epitope of the antibody can be isolated from the whole antibody by chemical or mechanical disruption of the molecule. The purified fragments thus obtained can be tested to determine their immunogenicity and specificity by the methods taught herein. Immunoreactive epitopes of the antibody can also be synthesized directly. An immunoreactive fragment is defined as an amino acid sequence of at least about 5 consecutive amino acids derived from the antibody amino acid sequence.

One method of producing proteins comprising the antibodies of the present invention is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert butyloxycarbonoyl) chemistry. (Applied Biosystems, Inc., Foster City, Calif.). One skilled in the art can readily appreciate that a peptide or polypeptide corresponding to an antibody can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant, G. A., "Synthetic Peptides: A User Guide" W.H. Freeman and Co., N.Y. (1992) and Bodansky, M. and Trost, B., Ed., "Principles of Peptide Synthesis" Springer-Verlag Inc., N.Y. (1993)). Alternatively, the peptide or polypeptide can by independently synthesized in vivo as described above. Once isolated, these independent peptides or polypeptides may be linked to form an antibody or fragment thereof via similar peptide condensation reactions.

For example, enzymatic ligation of cloned or synthetic peptide segments can allow relatively short peptide fragments to be joined to produce larger peptide fragments, polypeptides or whole protein domains (Abrahmsen, L., et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson, et al., "Synthesis of Proteins by Native Chemical Ligation" Science, 266:776-779 (1994)). The first step is the chemoselective reaction of an unprotected synthetic peptide-α-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Clark-Lewis, L, et al., FEBS Lett., 307: 97 (1987), Clark-Lewis, L, et al., J. Biol. Chem., 269:16075 (1994), Clark-Lewis, L, et al., Biochemistry, 30:3128 (1991), and Rajarathnam, K, et al., Biochemistry, 29:1689 (1994)).

Alternatively, unprotected peptide segments can be chemically linked where the bond formed between the peptide segments as a result of the chemical ligation is an unnatural (non-peptide) bond (Schnolzer, M., et al., Science, 256:221 (1992)). This technique has been used to synthesize analogs of protein domains as well as large amounts of relatively pure proteins with full biological activity (deLisle Milton, R. C., et al., "Techniques in Protein Chemistry IV" Academic Press, New York, pp. 257-267 (1992)).

The invention also provides fragments of antibodies which have bioactivity. The polypeptide fragments of the present invention can be recombinant proteins obtained by cloning nucleic acids encoding the polypeptide in an expression system capable of producing the polypeptide fragments thereof, such as the adenovirus system described herein. For example, one can determine the active domain of any of the antibodies described herein which can cause a biological effect associated with the interaction of the antibody with the hepatocyte growth factor. Amino acids found to not contribute to either the activity or the binding specificity or affinity of the antibody can be deleted without a loss in the respective activity.

For example, amino or carboxy-terminal amino acids can be sequentially removed from either the native or the modified non-immunoglobulin molecule or the immunoglobulin molecule and the respective activity assayed in one of many available assays. In another example, a fragment of an antibody can comprise a modified antibody wherein at least one amino acid has been substituted for the naturally occurring amino acid at a specific position, and a portion of either amino terminal or carboxy terminal amino acids, or even an internal region of the antibody, has been replaced with a polypeptide fragment or other moiety, such as biotin, which can facilitate in the purification of the modified antibody. For example, a modified antibody can be fused to a maltose binding protein, through either peptide chemistry or cloning the respective nucleic acids encoding the two polypeptide fragments into an expression vector such that the expression of the coding region results in a hybrid polypeptide. The hybrid polypeptide can be affinity purified by passing it over an amylose affinity column, and the modified antibody receptor can then be separated from the maltose binding region by cleaving the hybrid polypeptide with the specific protease factor Xa. (See, for example, New England Biolabs Product Catalog, 1996, pg. 164.). Similar purification procedures are available for isolating hybrid proteins from eukaryotic cells as well.

The fragments, whether attached to other sequences or not, can also include insertions, deletions, substitutions, or other selected modifications of particular regions or specific amino acids residues, provided the activity of the peptide is not significantly altered or impaired compared to the nonmodified antibody or antibody fragment. These modifications can provide for some additional property, such as to remove/add amino acids capable of disulfide bonding, to increase its bio-longevity, to alter its secretory characteristics, etc. In any case, the peptide must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the receptor. (Zoller, M. J. et al.).

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab' or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986), Reichmann et al., Nature, 332: 323-327 (1988), and Presta, Curr. Op. Struct. Biol., 2:593-596 (1992)).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525 (1986), Riechmann et al., Nature, 332:323-327 (1988), Verhoeyen et al., Science, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody (Sims et al., J. Immunol., 151:2296 (1993) and Chothia et al, J. Mol. Biol., 196:901 (1987)). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding (see, WO 94/04679 published 3 Mar. 1994).

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits et al., Proc. Natl. Acad. Sci. USA, 90:2551-255 (1993); Jakobovits et al., Nature, 362:255-258 (1993); Bruggermann et al., Year in Immuno., 7:33 (1993)). Human antibodies can also be produced in phage display libraries [Hoogenboom et al., J. Mol. Biol., 227:381 (1991); Marks et al., J. Mol. Biol., 222:581 (1991)]. The techniques of Cote et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)].

The antibodies of this invention can be used as reagents and as research tools to detect HGF and to detect cells and tissues that express HGF. The antibodies can also be utilized in competitive binding assays to screen for and identify compounds that bind to HGF.

The present invention further provides a kit for detecting the binding of an antibody to the hepatocyte growth factor. Particularly, the kit can detect the presence of a hepatocyte growth factor specifically reactive with the antibody or an immunoreactive fragment thereof. The kit can include an antibody bound to a substrate, a secondary antibody reactive with the antigen and a reagent for detecting a reaction of the secondary antibody with the antigen. Such a kit can be an ELISA kit and can comprise the substrate, primary and secondary antibodies when appropriate, and any other necessary reagents such as detectable moieties, enzyme substrates and color reagents as described above. The diagnostic kit can, alternatively, be an immunoblot kit generally comprising the components and reagents described herein.

The present invention also provides a method of treating cancer in a subject comprising administering to the subject a combination of anti-HGF/SF antibodies, whereby the antibodies bind to a hepatocyte growth factor, whereby the binding of the antibodies to a hepatocyte growth factor results in an inhibition of hepatocyte growth factor binding to the hepatocyte growth factor receptor, whereby the inhibition of hepatocyte growth factor binding to receptor causes an inhibition of cancer growth, thereby treating the cancer.

One skilled in the art could identify combinations of anti-HGF/SF antibodies that inhibit or neutralize HGF/SF binding to hepatocyte growth factor by testing combinations of anti-HGF/SF antibodies for inhibiting or neutralizing activity in an MDCK scatter assay. For example, the skilled artisan would contact MDCK cells with HGF and a combination of anti-HGF/SF antibodies, as described in the Examples, and microscopically visualize the MDCK cells. If a particular combination of anti-HGF/SF antibodies inhibits or neutralizes HGF/SF activity (e.g. scattering), the MDCK cells will not exhibit significant scattering behavior and will be comparable in number and morphology to MDCK cells in the absence of HGF. An example of the microscopic differences between antibody combinations that neutralize HGF/SF and antibodies that do not is clearly illustrated in FIG. 1. The neutralizing activity of an antibody combination can be confirmed by performing branching morphogenesis assays with other cell types such as SK-LMS-1 cells and ARZ-2 human renal carcinoma cells, as described in the Examples. Briefly, the cells are mixed with Matrigel and plated, HGF/SF or HGF/SF and a combination of anti-HGF/SF antibodies is added and the cells are then visualized to determine the extent of branching morphogenesis. If a particular combination of anti-HGF/SF antibodies inhibits or neutralizes HGF/SF activity, the cells will not branch significantly and will appear similar in number and morphology to cells in the absence of HGF/SF. Therefore, the MDCK scatter assay and the branching morphogenesis assay can also be combined to identify effective combinations of anti-HGF/SF antibodies.

As used herein, "treating" or "treatment" means partial or total killing of cancerous cells, reduction in tumor size, inhibition of tumor growth, inhibition of vascularization, inhibition of cellular proliferation, an induction in dormancy or an apparent induction of dormancy, or a decreased metastasis of a tumor or a tumor cell.

The terms "cancer," "carcinoma," and "cancerous" when used herein refer to or describe the physiological condition, preferably in a mammalian subject, that is typically characterized by unregulated cell growth. Examples of types of cancer include but are not limited to, carcinoma, lymphoma, sarcoma, blastoma and leukemia. More particular examples of such cancers include squamous cell carcinoma, lung cancer, pancreatic cancer, cervical cancer, bladder cancer, kidney cancer, gliobastoma, hepatoma, breast cancer, prostate carcinoma, colon carcinoma, head cancer, neck cancer rhabdomyosarcoma, osteosarcoma, leiomysarcoma, myelogenous leukemia, lymphocytic leukemia, multiple myeloma, Hodgkins lymphoma, and B-cell lymphomas. While the term "cancer" as used herein is not limited to any one specific form of the disease, it is believed that the methods of the invention will be particularly effective for cancers which are found to be accompanied by increased levels of HGF or expression of Met. Examples of such cancers include, but are not limited to, lung cancer, pancreatic cancer, bladder cancer, kidney cancer, gioblastoma, prostate cancer, osteosarcoma and soft tissue sarcoma.

The antibodies are preferably administered to the subject, patient, or cell in a pharmaceutically-acceptable carrier. Suitable carriers and their formulations are described in Remington's Pharmaceutical Sciences, 16th ed., 1980, Mack Publishing Co., edited by Oslo et al. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. The antibodies may also be administered by intratumoral, peritumoral, intralesional, or perilesional routes, to exert local as well as systemic therapeutic effects. Local or intravenous injection is preferred.

Effective dosages and schedules for administering the antibodies may be determined empirically, and making such determinations is within the skill in the art. Those skilled in the art will understand that the dosage of antibodies that must be administered will vary depending on, for example, the mammal which will receive the antibody, the route of administration, the particular type of antibody used and other drugs being administered. Guidance in selecting appropriate doses for antibodies is found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of the antibody used alone might range from about 1 µg/kg to up to 100 mg/kg of body weight or more per day, depending on the factors mentioned above. For example, a typical antibody dosage range could be 1 mg/kg to 8 mg/kg as described in Tokuda et al. ("Dose escalation and pharmacokinetic study of a humanized anti-HER2 monoclonal antibody in patients with HER2/neu-overexpressing metastatic breast cancer" Br. J. Cancer 81: 1419-1425 (1999).

The antibodies may also be administered in combination with effective amounts of one or more other therapeutic agents or in conjunction with radiation treatment. Therapeutic agents contemplated include chemotherapeutics as well as immunoadjuvants and cytokines. Chemotherapies contemplated by the invention include chemical substances or drugs which are known in the art and are commercially available, such as Doxorubicin, 5-Fluorouracil, Cytosine arabinoside ("Ara-C"), Cyclophosphamide, Thiotepa, Busulfan, Cytoxin, Taxol, Methotrexate, Cisplatin, Melphalan, Vinblastine and Carboplatin. The antibodies may be administered sequentially or concurrently with the one or more other therapeutic agents. The amounts of antagonist and therapeutic agent depend, for example, on what type of drugs are used, the condition being treated, and the scheduling and routes of administration but would generally be less than if each were used individually. Following administration of antibodies, the condition can be monitored in various ways well known to the skilled practitioner. For instance, tumor mass may be observed physically or by standard x-ray imaging techniques.

The present invention further provides a method of screening a subject for the presence of a developmental disorder comprising: contacting a tissue sample from the subject with a combination of anti-HGF/SF antibodies, detecting the binding of the antibodies with an antigen in the tissue sample, whereby a reduction in binding of antigen to the antibodies in the tissue sample relative to the binding of antigen from a control tissue sample to the antibodies indicates a decreased amount of hepatocyte growth factor in the sample, whereby the reduction in the amount of hepatocyte growth factor indicates a developmental disorder is present in the patient, thereby screening the subject for the presence of a developmental disorder. Binding of antigen to antibody can be measured by methods known in the art and as described in the Examples, such as by ELISA, immunohistochemistry or Western blot.

The sample of this invention can be from any organism and can be, but is not limited to, peripheral blood, bone marrow specimens, primary tumors, embedded tissue sections, frozen tissue sections, cell preparations, cytological preparations, exfoliate samples (e.g., sputum), fine needle aspirations, amnion cells, fresh tissue, dry tissue, and cultured cells or tissue. The sample can be unfixed or fixed according to standard protocols widely available in the art and can also be embedded in a suitable medium for preparation of the sample. For example, the sample can be embedded in paraffin or other suitable medium (e.g., epoxy or acrylamide) to facilitate preparation of the biological specimen for the detection methods of this invention. Furthermore, the sample can be embedded in any commercially available mounting medium, either aqueous or organic.

The sample can be on, supported by, or attached to, a substrate which facilitates detection. A substrate of the present invention can be, but is not limited to, a microscope slide, a culture dish, a culture flask, a culture plate, a culture chamber, ELISA plates, as well as any other substrate that can be used for containing or supporting biological samples for analysis according to the methods of the present invention. The substrate can be of any material suitable for the purposes of this invention, such as, for example, glass, plastic, polystyrene, mica and the like. The substrates of the present invention can be obtained from commercial sources or prepared according to standard procedures well known in the art.

The present invention also provides a method of in vivo detection of the HGF/SF antibody combinations comprising administering the HGF/SF antibodies conjugated to a tracer to a subject and imaging the antibodies. Tracers that may be conjugated to the antibodies are known in the art and include radiolabels such as 99mTc, 111In, 125I, 131I. Imaging techniques are also known in the art and include immunoscintography, single photon emission computed tomographic imaging and high-resolution gamma-camera imaging (Sato et al. 1999. "Intratumoral distribution of radiolabeled antibody and radioimmunotherapy in experimental liver metastases model of nude mouse" J. Nucl. Med. 40:685-692; Reilly 1993 "Immunoscintography of tumours using 99Tcm-labelled monoclonal antibodies: a review" Nucl. Med. Commun. 14:347-359.) One skilled in the art would be able to select the appropriate combination of tracer and imaging technique to detect the HGF/SF antibodies in vivo.

The in vivo imaging of the HGF/SF antibody combinations can be utilized for diagnostic purposes, prognostic purposes as well as for the intraoperative detection of metastatic deposits.

One skilled in the art will appreciate that the HGF/Met pathway is involved in fundamental biological activities such as the formation of tubules and lumens, the promotion of angiogenesis, the inhibition of cell growth, and the conversion from a mesenchymal to an epithelial phenotype. In vivo, this ligand-receptor pair is believed to play a role in neural induction, kidney development, tissue regeneration, wound healing, and is required for normal embryological development. Therefore the levels of HGF in a tissue sample can indicate the status of the cell with respect to its developmental state. One skilled in the art will appreciate that the monoclonal antibodies provided by this invention can be used in many detection procedures to detect and quantitate the levels of HGF in the cell or tissue, and therefore screen a patient or subject for the presence of a developmental disorder. Additionally, the HGF/Met pathway is required for normal embryological development and decreased levels of HGF can result in defective organogenesis resulting in developmental abnormalities. In one embodiment of the present invention, the developmental disorder comprises those conditions resulting from an abnormal epithelial-mesenchymal cell conversion.

Further provided by the present invention is a method of detecting the presence of cancer in a patient comprising: contacting a tissue sample from the subject with a combination of anti-HGF/SF antibodies, detecting the binding of the antibodies with an antigen in the sample, whereby an increased binding of antigen to the antibodies relative to the binding of antigen from a control tissue sample to the antibodies indicates an increased amount of hepatocyte growth factor in the sample, whereby the increased amount of hepatocyte growth factor indicates the presence of cancerous tissue in the sample, thereby detecting the presence of cancer in the patient.

Also provided by the present invention is a method of determining the progression of cancer comprising: contacting a tissue sample from a patient having a cancer with a combination of anti-HGF/SF antibodies, detecting the binding of the antibodies with an antigen, measuring the amount of antigen in the sample, and correlating the binding of the antibodies with the antigen with a particular stage of cancer development, thereby determining the progression of cancer in the patient.

Since therapy and clinical decisions are often dependent on diagnosis, HGF detection with this antibody allows correlation of HGF expression levels with a particular stage of cancerous development. One skilled in the art would be able to measure HGF in numerous subjects in order to establish ranges of HGF expression that correspond to clinically defined stages of cancerous development. The process of determining the clinical stages of cancer are well defined for most cancers in the literature. These ranges will allow the skilled practitioner to measure HGF in a subject diagnosed with cancer and correlate the levels in each subject with a range that corresponds to a stage of cancer. One skilled in the art would also know that by measuring HGF in the patient at different intervals, the progression of the cancer can be determined. For example, if the patient is assayed for the presence of HGF at a first time point and the amount of HGF increases when the patient is assayed at a second time point, the skilled artisan would know the cancer has progressed. If the HGF decreases when the patient is assayed at a second time point, the skilled practitioner would know the cancer has not progressed. Treatment regimens can, therefore, be adjusted correspondingly.

A person skilled in the art would know that the methods of this invention can be utilized to test the efficacy of anticancer treatment. For example, if the patient diagnosed with cancer is assayed for the presence of HGF prior to the administration of an anticancer treatment and assayed at a second time point after the administration of the anticancer treatment, a decrease in the level of HGF may indicate an effective anticancer treatment had been administered. The skilled practitioner will associate the decreases observed with a particular level of effectiveness. If no decrease is observed, the anticancer treatment may need to be adjusted.

Numerous examples are present in the art for diagnosing and prognosticating HGF/SF related disorders by detecting HGF/SF (Shikano et al. 2000 "Usefulness of serum hepatocyte growth factor for the diagnosis of amyloidosis" Intern Med. 39: 715-719; Ohnishi et al. 2000. "Development of highly senstitive enzyme-linked immunosorbent assays for hepatocyte growth factor/scatter factor (HGF/SF): determination of HGF/SF in serum and urine from normal human subjects" J. Immunol. Methods 244: 163-173; Malatino et al. 2000. "Hepatocyte growth factor predicts survival and relates to inflammation and intima media thickness in end-stage renal disease" Am. J. Kidney Dis. 36: 945-52; Gohji et al. 2000. "Independent prognostic value of serum heptocyte growth factor in bladder cancer" J. Clin. Oncol. 18: 2963-71;

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the claims included herein.

EXAMPLE I

Anti-HGF/SF Antibody Production

Murine anti-HGF/SF monoclonal antibodies (Mab) were developed by fusion of the OUR-1 myeloma cell line obtained from the American Type Culture Collection (ATCC) with spleen cells of a Balb/C mouse hyper-immunized with native HGF/SF. The fusion was performed when the mouse serum displayed positive neutralizing activity. ELISA positive hybridomas were re-cloned, and neutralizing activity was first screened in the MDCK cell scatter assay. Eight hybridoma cell lines were selected and ascites were produced and purified by FPLC protein-G column (Table 1).

MDCK Scattering Assay

No single Mab showed significant inhibition of HGF/SF mediated scattering activity in Madin-Darby canine kidney (MDCK) cells while pooled Mabs inhibited MDCK scattering. Whether or not it was possible for a specific sub-set of the Mabs to efficiently neutralize HGF/SF activity was determined. Combinations of two or three of the antibodies were tested and it was determined that antibodies 1+4+7; 1+5+7; 1+4+10 or 1+5+10 were able to block HGF/SF activity at low antibody concentration in the branching morphogenesis assay (Table 1). However, 1+5+7 displayed the strongest neutralizing activity when tested in the in vitro invasion assay (Table 2). Thus, in in vitro invasion assays using ARZ-2 renal carcinoma cells (6), individual Mab did not inhibit HGF/SF activity 1+5+7 completely abolished the activity. Importantly, as little as 5/g of total IgG was able to completely neutralize 1 μg of HGF/SF. The combination of antibodies 1+5+7 is able to inhibit HGF/SF mediated MDCK cells scattering or ARZ-2 renal carcinoma cell in vitro invasion.

Antibody Interference Mapping Studies

Mapping studies by antibody interference mapping (AIM) (Table 3) were also performed. These analyses reveal the interference pattern of Mabs and are consistent with the neutralizing activity. Thus, antibodies #1, 5, and 7 can be used together as a strong HGF/SF inhibitor.

The anti-HGF/SF Mabs were found to be useful in ELISA assays (Table 4). Moreover, the reactivity of the five individual Mabs was characterized by ELISA against either the whole HGF/SF molecule or the a-subunit NK2 domain (Table 4). These studies show that #1, 4, 5, 7, and 10 are reactive against HGF/SF, but only #1 and 5 are reactive to NK2 and #7 shows a 10 fold lower reactivity against NK2 vs. HGF/SF.

The anti-HGF/SF Mabs are also very useful for immunohistochemical staining and very effective in immunoprecipitation analyses.

Antitumor Activity

Several combinations of anti-HGF/SF antibodies provided by this invention were tested and found to possess antitumor activity in a mouse model tumor system previously described by Jeffers et al.

EXAMPLE II

Cell Lines

MDCK cells were cultured in DMEM medium supplemented with 5% fetal bovine serum (FBS). S-114 cells (transformed with human HGF/SF and Met) (13) were grown in DMEM containing 8% of calf serum. ARZ-2 human renal carcinoma cell line (6) was maintained in DMEM containing 10% FBS. C-127 cell line is NIH 3T3 transformed with human HGF/SF and mouse Met (14), and U-118 cell line is established from human glioma that co-expresses HGF/SF and Met (11). Both cells were maintained in DMEM supplemented with 10% FBS. All cell lines were cultured at 37° C., 5% $CO_2$.

Immunization for Mab Production

Rabbit polyclonal antibody to HGF/SF was used as positive control. HGF/SF was prepared from S114 cells (15), and mouse Mabs against the ligand were produced by injecting Balb/C mice IP with purified native and denatured (by boiling in sodium dodecyl sulfate (SDS) sample buffer) HGF/SF protein in complete Freund's adjuvant, followed by four additional injections in incomplete Fruend's adjuvant. After one month, a final HGF/SF injection was given IP and IV without adjuvant. Polyclonal antisera from immunized mice were tested for HGF/SF specific antibodies by ELISA, and for neutralizing activity in the MDCK cell scatter assay. The serum from animals immunized with denatured HGF/SF never displayed neutralizing activity to HGF/SF in the scatter assay. Spleen cells were fused with P3X63AF8/653 myeloma cells using standard techniques three days after final injections.

ELISA Screening

Hybridoma cells were screened for reactivity to HGF/SF by ELISA using 96 well plates coated with 2.5 ug/ml of HGF/SF in coating buffer (0.2M $Na_2CO_3$/$NaHCO_3$, pH9.6, 50 μl/well) overnight at 4° C. The plates were then blocked with PBS containing 1% BSA (200 μl/well) for one hour at room temperature (RT) or overnight at 4° C. Fifty micro liters of hybridoma supernatant were added to wells for 1.5 hours at RT. Plates were washed two times in washing buffer (PBS with 0.05% Tween-20), and alkaline phosphatase coupled goat-anti-mouse IgG (Sigma) was added (50 μl/well) at 1:3,000 dilution for 1.5 hours at RT. After washing four times in washing buffer, phosphatase substrate CP-nitrophenylphosphate, purchased from Kirkegaard and Perry, was added for 30 min and absorbance was measured at 405 nm. Hybridomas with strong reactivity with HGF/SF (OD value greater than 0.5, negative controls lower than 0.02) were re-cloned twice, and reactivity was confirmed by ELISA.

HGF/SF Neutralization in the MDCK Scatter Assay

Re-cloned hybridomas supernatants, either individually or in pools, were tested for neutralizing activity to HGF/SF using the MDCK cell scatter assay. Briefly, MDCK cells were cultivated in DMEM with 5% FBS at 37° C., 5% $CO_2$ overnight. Three hundred micro liters of supernatants (either individually or as pools) were added to 96 well plates. Two fold serial dilutions were made with DMEM, 5% FBS. MDCK cells were trypsinized, re-suspended in culture medium and cell density was adjusted to $7.5 \times 10^5$/ml before plating (100 μl/well) and addition of HGF/SF (5 ng/well). Positive and negative control wells contained either MDCK cells only or HGF/SF with or without rabbit polyclonal neutralizing antiserum (1 μl/well). Plates were placed at 37° C. (5% $CO_2$) overnight; cells were then stained with 0.5% crystal violet, 50% ethanol (v/v) for 10 min at RT, and scattering was viewed using a light microscope. Ascites were prepared from the hybridoma cell lines showing the strongest neutralizing activity. The IgGs were purified from protein-G column and adjusted to a final Mab concentration of 2 mg/ml. Neutralizing activity in the MDCK scatter assay was tested for each or a combination of antibodies.

Branching Morphogenesis Assay

Semi-confluent SK-LMS-1 cell cultures were washed twice with PBS ($Ca^{++}$ and $Mg^{++}$ free) and 4 ml Trypsin-EDTA was added before the cultures were incubated for 5 minutes at 37° C. (6). After centrifugation (5 min, 1,000×g) at 4° C., $5 \times 10^4$ cells in 62.5 μl DMEM-10% FBS were mixed with an equal volume of nondiluted GFR-Matrigel on ice, placed at 125 μl per well in a 96 well culture plate, and incubated for 30 min in 10% $CO_2$ at 37° C. After incubation, 125 μl of DMED-10% FBS, alone or supplemented with HGF/SF, and with or without neutralizing Mabs at the indicated concentration, was placed on top of the gel. After 72 to 96 hours of incubation at 37° C., representative wells were photographed at 400× magnification.

Immunohistochemistry

S-114 cells expressing HGF/SF and Met were fixed in either formaldehyde or Acetone/Methanol (50/50, v/v) for 10 minutes at RT, air dried for 10 minutes, then incubated with test Mabs mixed with either rabbit anti-HGF/SF polyclonal antibody or C-28 rabbit anti-Met polyclonal antibody at 37° C. for one hour for co-localization analysis. Cells were washed two times with PBS, and incubated with goat anti-mouse FITC and goat anti-rabbit rhodmine conjugates for one hour at 37° C. The samples were observed by confocal microscopy.

HGF/SF Immunoprecipitation

S-114 cells (13, 15) expressing human HGF/SF and Met were grown in 75 $cm^2$ flask in serum free medium, and cultured for 48 hours at 37° C., 5% $CO_2$. The supernatant containing HGF/SF was centrifuged and pre-incubated with normal rabbit serum and protein-G beads for two hours on ice. After centrifugation, 1 ml of supernatant was reacted with each HGF/SF Mab (or control mouse IgG) with shaking at 4° C. for one hour. Twenty micro liters of protein-G beads (50%, v/v) was added to each tube and incubated at 4° C. overnight with shaking. The immune complexes were washed three times with PBS. Bound proteins were eluted by heating the beads to 95° C. for 10 min with 50 ul of 2×SDS sample buffer. The proteins were separated by 10% SDS-PAGE gel, and then transferred onto PVDF membrane (Bio-Rad). The membrane was blocked in 1% BSA/PBS (Sigma) overnight at 4° C., and incubated for 1.5 hours at RT in 1:4,000 diluted (blocking buffer) with rabbit polyclonal anti-HGF/SF antibody. After four washes (PBS containing 0.05% Tween-20), five minutes each, the membrane was reacted with goat anti-rabbit IgG alkaline phosphatase conjugate (1:10,000, sigma) for an additional 1.5 hours with shaking at RT. Following the same washing, the detection reagent, chemoilluminate substrate (Bio-Rad) was placed to the membrane.

Western Blot

Purified human HGF/SF (15) or the NK2 protein subunit were mixed with either SDS sample buffer or native buffer (Bio-Rad) and heated at 95° C. for ten minutes with 0.5 µg of HGF/SF or 0.4 µg of NK2 was loaded to each 4-15% gradient SDS-PAGE 2-D prep ready gel (Bio-Rad). Separated proteins were transferred to PVDF membrane and blocked with 1% BSA/PBS overnight at 4° C. The membrane was rinsed, dried and cut into test strips. Each Mab was diluted to 1:1,000 with blocking buffer and allowed to react for 1.5 hours at RT. After washing 4×, goat anti-mouse IgG alkaline phosphatase conjugate was added at 1:10,000 dilution and incubated 1.5 hours at RT. The strips were washed four times before the chemoilluminate substrate was added.

Antibody Interference Analysis

Each Mab was placed in the primary position for Biacor (Pharmacia) analyses, and the relative binding of each Mab in the panel of antibodies was evaluated. The mean signal due to non-self associating antibodies used both in primary and secondary positions were taken as the value for complete interference. When the sandwich signal was greater than two standard deviations above the complete interference level, the antibodies bind independently to human HGF/SF. When the signal is equal or less than the complete interference level, the two antibodies interfere.

Mab Inhibition of Tumor Growth in Athymic Nude Mice Tumor Activity

Animal experiments were performed using female athymic nude nu/nu mice at six weeks of age. Mab combinations (e.g. A.1, 5, 7) prepared against native HGF/SF were compared to non-neutralizing Mabs prepared against denatured HGF/SF.

C-127 cells expressing human HGF/SF and mouse Met were trypsinized, washed two times in PBS and re-suspended to $2\times10^6$ cells/ml in PBS. Mice were divided into five groups and five mice per group. Each mouse was injected s.c. with 0.1 ml of C-127 cell suspension ($2\times10^5$ cells per mouse). At day one post cell injection, antibodies were administered (100 µl/animal) at 2 mg/ml concentration. Group 1 animals were injected s.c. intra-tumor with the Mab A.1, 5 and 7. Group 2 animals were injected I.P. with the same Map pool. Groups 3 and 4 were injected with a combination of Mabs 7-2, 3, reactive with denatured HGF/SF, but non-neutralizing, and either s.c. or I.P. respectively. Group 5 animals received C-127 tumor cells, but no antibodies. The antibody injections were repeated everyday for 20 days, and tumor size was measured twice a week. The experiments were terminated when the control group needed to be sacrificed due to tumor size.

The U-118 cell line, a human glioblastoma multiforme tumor cell line was shown previously to express HGF/SF and Met (11). Cells were injected as follows: $5\times10^5$ U-118 cells were injected s.c. into seven mice per group. As in the C127 studies above, neutralizing Mab combination A.1, 5 and 7, and non-neutralizing Mab combination 7-2, 3 were injected twice a week (100 µl/animal of a 2 mg/ml Mab concentrate) until 10 weeks post cell injection, then all animals were terminated.

The tumor regression experiment was performed using the U-118 cell line. $5\times10^5$ cells were injected s.c. into each mouse for total 60 mice. At 30 days post cells injection, animals were divided to five groups, 10 mice per group with average tumor size about 100 mm$^3$. Neutralizing (A.1, 5, 7) and control (7-2, 3) Mab combinations were either s.c. (intra-tumor) or I.P. injected every two days (100 µl/mouse at 2 mg/ml Mab concentration) until 10 weeks.

Production of Mabs to hHGF/SF

Mabs were raised against both native and denatured HGF/SF. Serum from HGF/SF immunized mice was tested for neutralizing activity in the MDCK scatter assay, and only serum from mice immunized with native HGF/SF inhibited scattering. After fusion of spleen cells with P3X63AF8/653 myeloma cells, single clones of hybridoma cells reactive with HGF/SF were selected, and Mabs against native and denatured HGF/SP were tested individually for neutralizing activity in the MDCK scatter assay. None of the Mabs displayed activity. However, since the serum from the mice immunized with native HGF/SF displayed neutralizing activity, Mab culture supernatants were pooled to test for neutralization activity against HGF/SF. One group of 10 pooled Mabs (A.1-10) showed strong neutralizing activity to HGF/SF (Table 5). None of the pools of Mabs against denatured HGF/SF displayed neutralizing activity.

To further characterize the A.1-10 pool, ascites were produced individually and Mabs were purified on a protein-G column, adjusted to 2 mg/ml, and tested in various combinations to determine which members of the pool contributed to neutralizing activity (Table 5). It was found that combinations of any of two Mabs of A.1-10 did not neutralize scattering, even when Mabs were used at concentrations of micrograms of Mabs to nanograms of HGF/SF. However, when three or more Mabs were combined, seven different combinations were identified with significant neutralizing activity (<30:1, Table 5). A combination of four Mabs, which included A.1, and any three of Mabs A.4, 5, 7 or 10, had the highest activity. However, combinations of Mab A.1, plus either A.4 or 5 and 7 or 10, also efficiently neutralized HGF/SF mediated MDCK scatter activity with Mabs A.1, 5, 7 and/or A.1, 5, 10 showing the greatest neutralizing activity (Table 5, FIG. 1). The Mab "7" series in combination with the Mabs generated against denatured HGF/SF (7, 2, 3, 4) did not prevent scattering (FIG. 1).

Branching Morphogenesis

The neutralizing activity of the Mabs in the HGF/SF mediated branching morphogenesis assay was tested. Again, the Mab combination A.1, 5, 7 displayed the greatest inhibitory activity (Table 5, FIG. 2). However, A.4 or 5, with 7 or 10, also show significant activity, indicating that something provided by the basement membrane matrigel or the SKLMS-1 cells, excludes the requirement for Mab A.1.

Immunoprecipitation, Western Analyses and Immunohistochemistry with Anti HGF/SF Mabs Mabs were further characterized by immunohistochemistry analyses performed on S-114 NIH3T3 cells expressing both human HGF/SF and Met molecules. Cells were fixed with either acetone/methanol or formaldehyde. S-114 cells fixed in acetone/methanol and stained with Mab A.10 and rabbit anti-HGF/SF antibody, show colocalization of staining. Each of the Mabs A.1, 4, 5, 7 and 7-2, 3, 4 display similar colocalization of staining with the rabbit anti-HGF/SF serum, demonstrating their specificity to HGF/SF. Using the same fixation conditions, the Mabs to HGF/SF do not colocalize with the rabbit polyclonal antibody (C-28) staining to Met. Moreover, the neutralizing Mabs give a stronger signal in acetone/methanol fixed cells (Table 6). Mab 7-2 raised against denatured HGF/SF, and Mab A.10, were very effective for staining both acetone/methanol and formaldehyde fixed cells (Table 6). These neutralizing Mabs are also very effective for immunoprecipitating native HGF/SF from cell supernatants, while the Mabs to denatured HGF/SF do not. However, the neutralizing Mabs do not recognize denatured HGF/SF on Western analysis, while the 7 series Mabs to denatured HGF/SF work well.

Of all the Mabs directed to native HGF/SF, only Mab A.1 reacts with the N-terminal NK2 priority. To test for epitope differences, the Mabs were subjected to antibody interference analysis. By these analyses, the five neutralizing Mabs recognized at least four different HGF/SF epitopes, with Mabs 4 and 5 apparently reacting with the same epitope. These results show that Mab A.1 and either A.4 or A.5 with either A.7 or A.10, are required to efficiently neutralize HGF/SF activity.

Anti-Tumor Activity of the HGF/SF Neutralizing Mab Combination

Figure 3:
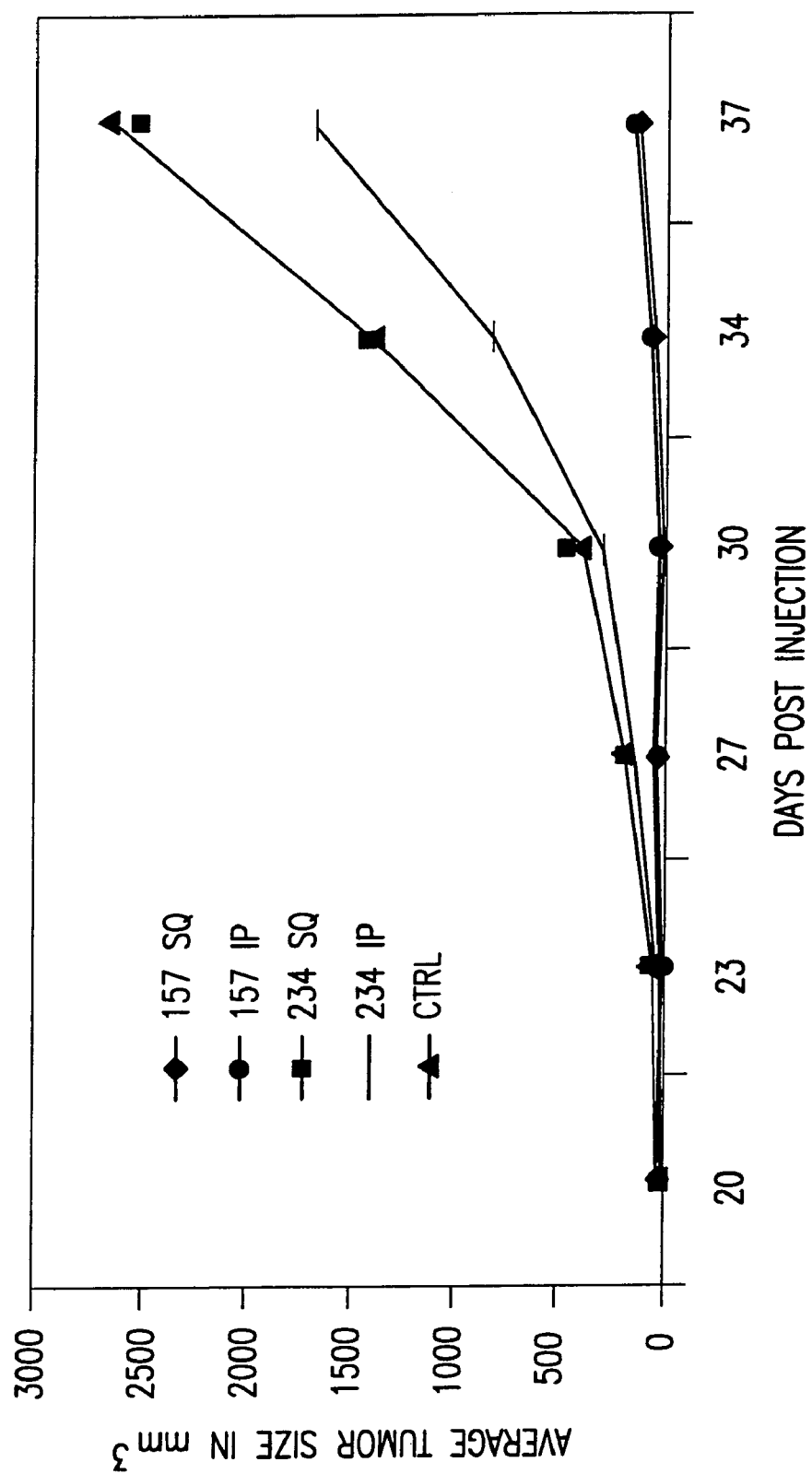
FIG. 3. Inhibition of C127 tumor growth by neutralizing Mab to HGF/SF. $2 \times 10^5$ C-127 tumor cells were injected s.c. into athymic nude mice in 100 ul PBS on day 0. Anti-hHGF/SF Mab A.1, 5, 7 or Mab 7-2, 3, 4 antibodies were administered either sub-cutaneously (intra-tumor) or i.p. every day for 20 days. One group of animals did not receive antibody. The values are an average of the size of five tumors in $mm^3$.

Cells with autocrine Met-HGF/SF signaling are tumorigenetic and metastastic in nude mice (14-17). There is also evidence for autocrine signaling of this ligand receptor pair in human tumors, such as human osteosarcomas and glioblastoma multiforme. To determine whether the neutralizing Mab to human HGF/SF has any effect on tumors in-vivo, animal experiments were performed with C-127 mouse cells created to express mouse MET and human HGF/SF in an autocrine fashion. These cells ($2 \times 10^5$) when injected S.C. formed tumors in athymic nude mice in two to three weeks. Animals injected with C-127 were also injected with either Mabs A.1, 5, 7, or 7-2, 3, 4, either s. c. or i. p. every day for 20 days. The experiment was terminated at 37 days post C-127 cell injection. Dramatically, the Mab A.1, 5, 7 treated animals showed 90% inhibition of tumor growth with either s.c. or i.p. Mab injection, compared to the controls (FIG. 3).

Figure 4:
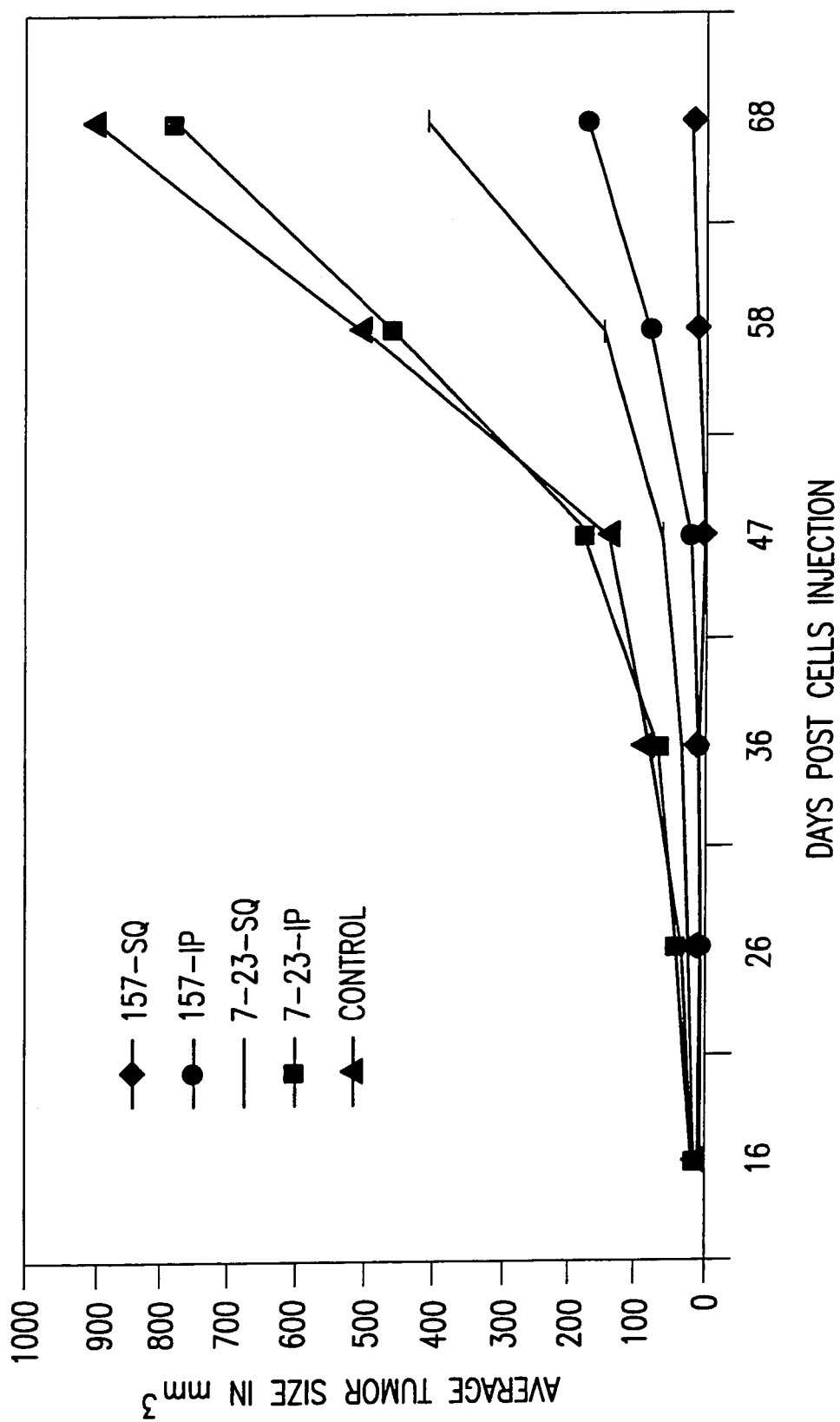
FIG. 4. Inhibition of U-118 glioblastoma tumor growth by neutralizing Mab to huHGF/SF. $5 \times 10^5$ U-118 human glioblastoma tumor cells were injected s.c. into athymic nude mice. On day 1, anti-HGF/SF Mab A.1, 5, 7 or Mab 7-2, 3 were administered either s.c. (intra-tumor) or i.p. twice a week for 10 weeks (70 days). One group of animals did not receive antibody. The values are an average size of 6-7 tumors (in $mm^3$).
Figure 5:
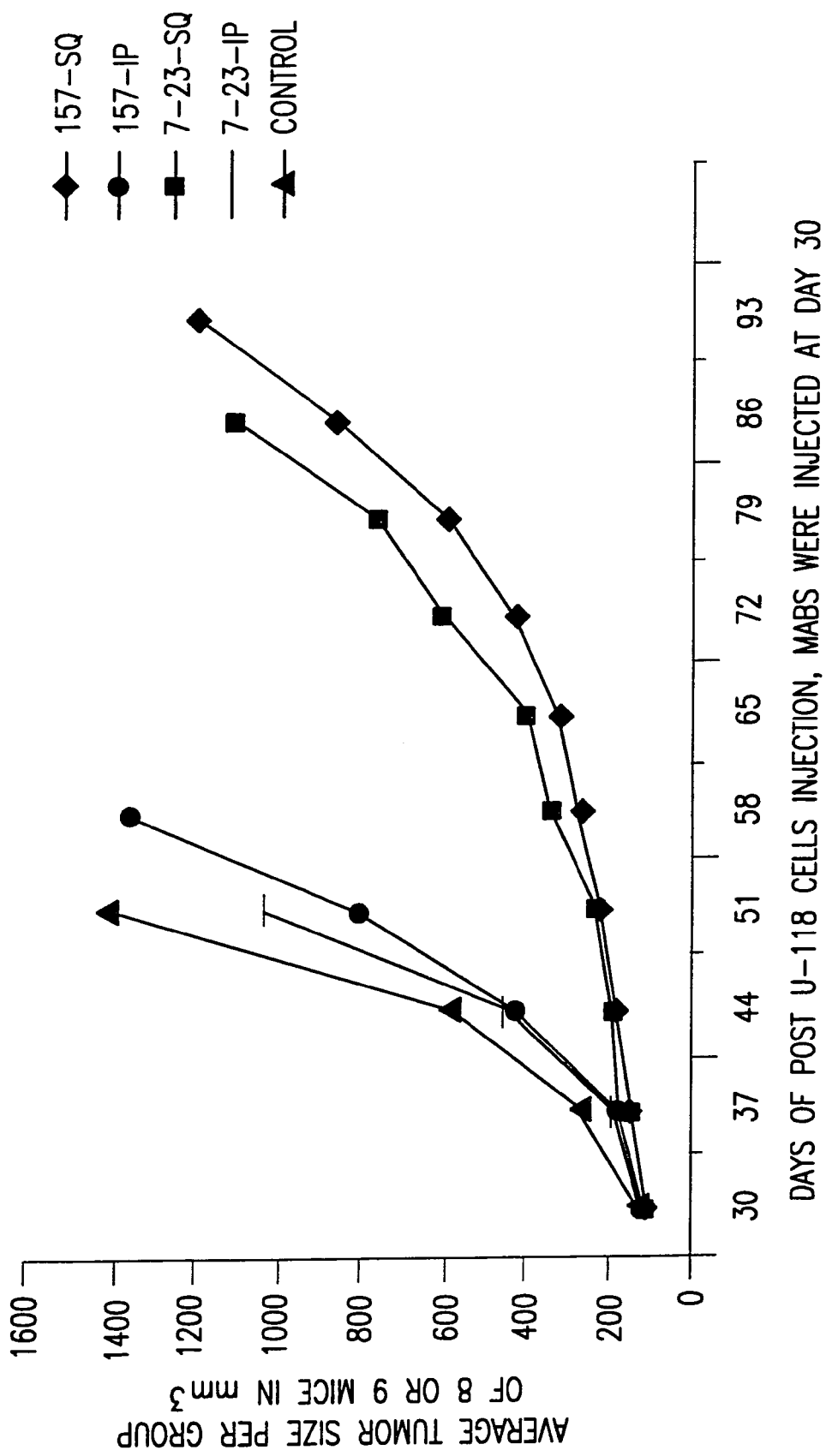
FIG. 5. Tumor regression experiment using U-118 GBM cells. $5 \times 10^5$ GBM cells were s.c. injected to athymic nude mice. After 30 days, animals were divided to 5 groups with average tumor size about 100 $mm^3$. MAb A.1, 5, 7 or 7-2, 3 were administered either s.c. (intra-tumor) or i.p. every two days until ten weeks. One group of mice did not receive antibody. The values are an average size of 8 to 9 tumors in $mm^3$.

Using the same procedure described above, the Mab A.1, 5, 7 combination was tested in-vivo versus the U-118 GBM tumor cells. Human glioma cell lines co-express HGF/SF and Met which are postulated to contribute to tumorigenesis. In this experiment, Mabs were injected two times in one week for 70 days. Intra-tumor (s.c.) injection of the neutralizing Mab combination completely inhibited tumor growth. While i.p. injection was less effective, the average tumor size of this group was diminished compared to the control groups (FIG. 4). Moreover, in animals in which Mab treatment was initiated 30 days after the U-118 GBM tumor cells were injected subcutaneously, a significant delay in tumor growth was observed in the animals receiving Mab A.1, 5, 7 every other day for up to 70 days. While tumor regression did not occur, tumor growth was reduced (FIG. 5).

Throughout this application various publications are referenced. The disclosures of all of these publications and those references cited within those publications in their entireties are hereby incorporated by reference into this application in order to more fully describe the state of the art to which this invention pertains.

REFERENCES

1. Matsumoto, K., et al. (1998) J. Biol. Chem. 273:22913-22920.
2. Hartmann, G., et al. (1992) Proc. Natl. Acad. Sci. U.S.A. 89:11574-11578.
3. Matsumoto, K., et al. (1991) Biochem. Biophys. Res. Commun. 181:691-69S.
4. Okigaki, M., et al. (1992) Biochem. 31:9555-9561.
5. Lokker, N. A. and P. J. Godowski (1993) J. Biol. Chem. 268:17145-17150.
6. Koochekpour, S., et al. (1999) Mol. Cell. Biol. 19: (In Press).
7. Sonnenberg, E., et al. (1993) J. Cell Biol. 123:223-235.
8. Grant, D. S., et al. (1993) Proc. Natl. Acad. Sci. U.S.A. 90:1937-1941.
9. Uehara, Y. and N. Kitamura (1992) J. Cell Biol. 117:889-894.
10. Nakamura, T. (1991) Prog. Growth Factor Res. 3:67-85.
11. Koochekpour, S., et al. (1997) Cancer Res. 57:5391-5398.
12. Rong, S., et al. (1994) Proc. Natl. Acad. Sci. U.S.A. 91:4731-4735.
13. Rong S, Bodescot M, Blair D, Dunn J, Nakamura T, Mizuno K, Park M, Chan A, Aaronson S, Vande Woude G F (1992) Mol Cell Biol 12:5152-5158.
14. Jeffers M, Rong S, Anver M, Vande Woude G F (1996) Oncogene 13:853-861.
15. Rong S, Oskarsson M, Faletto D, Tsarfaty I, Resau J H, Nakamura T, Rosen E, Hopkins R F 3d, Vande Woude G F (1993) Cell Growth Differ 4:563-9.
16. Jeffers M, Rong S, Vande Woude G F (1996) J. Mol. Med. 74:505-513.
17. Rong S, Segal S, Anver M, Resau J H, Vande Woude G F (1994) Proc. Natl. Acad. Sci. USA 91:4731-4735.

TABLE 1

The effect of monoclonal antibodies on branching morphogenesis of ARZ-2 renal carcinoma cell line[a]

| | $20/1^{c/d}$ | 10/1 | 5/1 | 1/1 |
|---|---|---|---|---|
| Neg. CTRL | − | − | − | − |
| Pos. CTRL | ++++ | ++++ | ++++ | ++++ |
| PolyAb CTRL[b] | − | − | − | − |
| 1 | ++++ | ++++ | ++++ | ++++ |
| 5 | ++++ | ++++ | ++++ | ++++ |
| 7 | ++++ | ++++ | ++++ | ++++ |
| 1 + 5 | ++ | +++ | ++++ | ++++ |
| 1 + 7 | ++ | +++ | ++++ | ++++ |
| 5 + 7 | − | − | − | + |
| 1 + 4 + 7 | + | + | ++ | +++ |
| 1 + 5 + 7 | − | − | − | + |
| 1 + 4 + 10 | + | + | ++ | +++ |
| 1 + 5 + 10 | + | + | ++ | +++ |
| Pooled | + | + | +++ | +++ |

[a]Branching morphogenesis was performed according to standard protocol (11).
[b]Rabbit polyclonal neutralizing anti-HGF antibody was used as positive control antibody for inhibition of branching morphogenesis.
[c]Nanogram per ml of anti-HGF neutralizing antibody.
[d]Nanogram per ml of HGF.

TABLE 2

The effect of monoclonal antibodies on Renal Carcinoma cells invasion through Matrigel coated filters[a]

|  | 20/1[b/c] | 10/1 | 5/1 | 1/1 |
|---|---|---|---|---|
| −HGF (Neg.) | 800 + 39[d] | ND[e] | ND | ND |
| +HGF (Pos.) | 2100 + 76 | ND | ND | ND |
| MAb 1 | 2190 + 83 | 2146 + 74 | 2216 + 53 | 1970 + 54 |
| MAb 5 | 1935 + 67 | 2112 + 69 | 2164 + 66 | 2212 + 71 |
| MAb 7 | 2186 + 75 | 2040 + 81 | 1996 + 59 | 2200 + 82 |
| MAb 5 + 7 | 1116 + 64 | 1272 + 52 | 1340 + 44 | 1766 + 51 |
| Mab 1 + 5 + 7 | 1064 + 46 | 1186 + 45 | 1224 + 41 | 1643 + 47 |

[a]Invasion assay was performed on ARZ-2 renal carcinoma cell line according to the standard protocol (6).
[b]Nanogram per ml of anti-HGF neutralizing antibody in lower chamber of transwell filter.
[c]Nanogram per ml of HGF in lower chamber of transwell filter.
[d]Each value represent the total number of cells invaded per filter and is the average of three independent experiments + SE.
[e]Not done

TABLE 3

Epitope Mapping by Antibody Interference (Pseudo-affinity analysis method)

| Pri./Sec. | 1 | 4 | 5 | 7 | 10 |
|---|---|---|---|---|---|
| 1 | 0.328 | 6.045 | 13.096 | 13.372 | 31.924 |
| 4 | 9.067 | 0.341 | 1.674 | 4.28 | 14.923 |
| 5 | 17.571 | 0.327 | 1.065 | 11.016 | 22.315 |
| 7 | 89.378 | 62.237 | 57.936 | 6.692 | 147.184 |
| 10 | 22.715 | 16.655 | 27.800 | 14.821 | 4.55 |

Each antibody in turn is placed in the primary position, and the relative binding of each antibody in the panel of antibodies in the sandwich is evaluated. The mean signal due to all non-self associating antibodies used as both the primary and secondary positions are taken as the value for complete interference. When the sandwich signal is greater than two standard deviations above the complete interference level, two antibodies binding independently to the HGF/SF, when signal is equal to or less than the complete interference level, the two antibodies interfere. The above data showed that antibodies 1, 7 and 10 recognize different epitopes of HGF/SF, 4 and 5 interference each other and recognize other epitope of HGF/SF.

TABLE 4

MABs Epitope Mapping by ELISA

| MAb# | Hybridoma I.D. | ELISA OD Anti-hHGF | ELISA OD Anti-HGF/NK2 |
|---|---|---|---|
| 1 | 1C10-F1-A11 | 1.941 | 3.105 |
| 4 | 8H2-F2-B10 | 2.432 | 0.043 |
| 5 | 13B1-E4-E10 | 2.934 | 1.807 |
| 7 | 15D7-B2 | 3.372 | 0.420 |
| 10 | 31D4-C9-D4 | 2.779 | 0.000 |

All of five antibodies showed high positive activity against the HGF/SF whole molecule. Mabs 1, 5 and 7 are able to recognize NK2 domain with significantly decreased affinity for 5 and 7 and increased affinity for 1. Mabs 4 and 10 do not bind to NK2.

TABLE 5

Inhibition of HGF/SF induced MDCK cells scattering and SK-LMS-1 cells branching morphogenesis by monoclonal antibody combinations. MDCK cell scatter assay: Each Mab combination was 2 fold diluted from well #1 to well #12 in 96 well plate (150 µl/well) with DMEM medium, hHGF/SF was adjusted to 5 ng in 100 µl cell suspension (final concentration was 20 ng/ml). Positive controls were MDCK cells only, and hHGF/SF with rabbit polyclonal neutralizing antibody. Negative control was MDCK cells with hHGF/SF only. Cells were fixed and stained prior to photography. SK-LMS-1 cells branching morphogenesis assay: hHGF/SF was used at 250 ng/ml, Mab combinations were from 1, 2, 4, 8 and 16 ug/ml. Result was read and photographed after 96 hours incubation.

| Mabs Combination | Mabs:huHGF/SF (Molar ratio) | |
|---|---|---|
|  | MDCK Cells Scattering | Branching Morphogenesis |
| Pool A (10 Mabs) | 80:1 | ND |
| Pool B (10 Mabs) | Neg. | ND |
| Pool C (11 Mabs) | Neg. | ND |
| A.1,4,5,7,10 | 24:1 | 10:1 |
| A.1,4,5,7 | 20:1 | 10:1 |
| A.1,4,5,10 | 20:1 | 10:1 |
| 1,4,7,10 | 20:1 | 10:1 |
| A.1,5,7,10 | 20:1 | 10:1 |
| A.1,4,5 | Neg. | Neg. |
| A.1,4,7 | 60:1 | 40:1 |
| A.1,4,10 | 60:1 | 20:1 |
| A.1,5,7 | 30:1 | 10:1 |
| A.1,5,10 | 30:1 | 10:1 |
| A.1,7,10 | 240:1 | Neg. |
| A.4,5,7 | Neg. | 40:1 |
| A.4,5,10 | Neg. | 20:1 |
| A.4,7,10 | Neg. | 40:1 |
| A.5,7,10 | Neg. | 40:1 |

TABLE 6

The ability of neutralizing and control Mabs to stain fixed S-114 cells. S-114 cells were fixed either with Acetone/Methanol (50:50, v/v) line A, or formaldehyde line B. All Mabs were 2 mg/ml and used at 1:100 dilution. Goat anti-mouse IgG FITC conjugate was diluted at 1:16.

|  | A.1 | A.4 | A.5 | A.7 | A.10 | 7-2 | 7-3 |
|---|---|---|---|---|---|---|---|
| A | ++ | + | + | ++ | +++ | +++ | ++ |
| B | − | − | + | + | +++ | +++ | + |

What is claimed is:

1. A combination of anti-HGF/SF monoclonal antibodies comprising three or more anti-HGF/SF antibodies selected from the group consisting of: the monoclonal antibody produced from the hybridoma deposited under ATCC Accession No. PTA-3414, the monoclonal antibody produced from the hybridoma deposited under ATCC Accession No. PTA-3415, the monoclonal antibody produced from the hybridoma deposited-under ATCC Accession No. PTA-3416, the monoclonal antibody produced from the hybridoma deposited under ATCC Accession No. PTA-3413, and the monoclonal antibody produced from the hybridoma deposited under ATCC Accession No. PTA-3412.

2. The combination of claim 1, comprising the antibody produced from the hybridoma deposited under ATCC Accession No. PTA-3414, the antibody produced from the hybridoma deposited-under ATCC Accession No. PTA-3416 and the antibody produced from the hybridoma deposited under ATCC Accession No. PTA-3413.

3. The combination of claim 1, comprising the antibody produced from the hybridoma deposited under ATCC Accession No. PTA-3414, the antibody produced from the hybridoma deposited under ATCC Accession No. PTA-3415 and the antibody produced from the hybridoma deposited under ATCC Accession No. PTA-3413.

4. The combination of claim 1, comprising the antibody produced from the hybridoma deposited under ATCC Accession No. PTA-3414, the antibody produced from the hybridoma deposited-under ATCC Accession No. PTA-3416 and the antibody produced from the hybridoma deposited under ATCC Accession No. PTA-3412.

5. The combination of claim 1, comprising the antibody produced from the hybridoma deposited under ATCC Accession No. PTA-3414, the antibody produced from the hybridoma deposited under ATCC Accession No. PTA-3415 and the antibody produced from the hybridoma deposited under ATCC Accession No. PTA-3412.

6. A combination of anti-HGF/SF monoclonal antibodies comprising three or more anti-HGF/SF antibodies selected from the group consisting of: the monoclonal antibody produced from the hybridoma deposited under ATCC Accession No. PTA-3414, the monoclonal antibody produced from the hybridoma deposited under ATCC Accession No. PTA-3415, the monoclonal antibody produced from the hybridoma deposited under ATCC Accession No. PTA-3416, the monoclonal antibody produced from the hybridoma deposited under ATCC Accession No. PTA-3413, and the monoclonal antibody produced from the hybridoma deposited under ATCC Accession No. PTA-3412, wherein the combination does not comprise both the monoclonal antibody produced from the hybridoma deposited under ATCC Accession No. PTA-3415 and the monoclonal antibody produced from the hybridoma deposited under ATCC Accession No. PTA-3416.

7. A combination of anti-HGF/SF antibodies comprising three or more anti-HGF/SF antibodies selected from the group consisting of: a monoclonal antibody that binds to the epitope bound by the antibody produced from the hybridoma deposited under ATCC Accession No. PTA-3414, a monoclonal antibody that binds to the epitope bound by the antibody produced from the hybridoma deposited under ATCC Accession No. PTA-3415, a monoclonal antibody that binds to the epitope bound by the antibody produced from the hybridoma deposited under ATCC Accession No. PTA-3416, a monoclonal antibody that binds to the epitope bound by the antibody produced from the hybridoma deposited under ATCC Accession No. PTA-3413, and a monoclonal antibody that binds to the epitope bound by the antibody produced from the hybridoma deposited under ATCC Accession No. PTA-3412.

8. A combination of anti-HGF/SF monoclonal antibodies comprising three or more anti-HGF/SF antibodies selected from the group consisting of: a monoclonal antibody that binds to the epitope bound by the monoclonal antibody produced from the hybridoma deposited under ATCC Accession No. PTA-3414, a monoclonal antibody that binds to the epitope bound by the monoclonal antibody produced from the hybridoma deposited under ATCC Accession No. PTA-3415, a monoclonal antibody that binds to the epitope bound by the monoclonal antibody produced from the hybridoma deposited under ATCC Accession No. PTA-3416, a monoclonal antibody that binds to the epitope bound by the monoclonal antibody produced from the hybridoma deposited under ATCC Accession No. PTA-3413, and a monoclonal antibody that binds to the epitope bound by the monoclonal antibody produced from the hybridoma deposited under ATCC Accession No. PTA-3412, wherein the combination does not comprise both a monoclonal antibody that binds to the epitope bound by the monoclonal antibody produced from the hybridoma deposited under ATCC Accession No. PTA-3415 and a monoclonal antibody that binds to the epitope bound by the monoclonal antibody produced from the hybridoma deposited under ATCC Accession No. PTA-3416.

* * * * *